(12) United States Patent
Zhang et al.

(10) Patent No.: US 8,110,353 B2
(45) Date of Patent: Feb. 7, 2012

(54) ENGINEERED TOEHOLD REACTIONS AND NETWORKS

(75) Inventors: David Zhang, Overland Park, KS (US); Andrew J. Turberfield, Oxford (GB); Erik Winfree, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 850 days.

(21) Appl. No.: 12/025,652

(22) Filed: Feb. 4, 2008

(65) Prior Publication Data

US 2009/0191546 A1 Jul. 30, 2009

Related U.S. Application Data

(60) Provisional application No. 60/899,546, filed on Feb. 5, 2007.

(51) Int. Cl.
*C12Q 1/68* (2006.01)
(52) U.S. Cl. .......... 435/6.1; 702/19; 536/23.1; 977/704; 977/711; 977/719; 977/941
(58) Field of Classification Search ................ None
See application file for complete search history.

(56) References Cited

U.S. PATENT DOCUMENTS

| | | | |
|---|---|---|---|
| 6,022,714 A | 2/2000 | Brown et al. | |
| 6,642,014 B1 | 11/2003 | Pedersen et al. | |
| 6,696,285 B1 | 2/2004 | Mills, Jr. et al. | |
| 2004/0062808 A1* | 4/2004 | Langrana et al. | 424/486 |
| 2007/0072215 A1* | 3/2007 | Seelig et al. | 435/6 |

OTHER PUBLICATIONS

Bath et al., "DNA nanomachines", Nature Nanotechnology, May 2007, vol. 2, pp. 276-284.
Benenson et al., "An autonomous molecular computer for logical control of gene expression", Nature, May 27, 2004, vol. 429, pp. 423-429.
Bois et al., "Topological constraints in nucleic acid hybridization kinetics", Nucleic Acids Research, 2005, vol. 33, No. 13, pp. 4090-4095.
Dirks et al., "Triggered amplification by hybridization chain reaction", PNAS, Oct. 26, 2004, vol. 101, No. 43, pp. 15275-15278.
Ellington et al., "In vitro selection of RNA molecules that bind specific ligands", Nature, Aug. 30, 1990, vol. 346, pp. 818-822.
Goodman et al., "Rapid Chiral Assembly of Rigid DNA Building Blocks for Molecular Nanofabrication", Science, Dec. 9, 2005, vol. 310, pp. 1661-1665.
Green et al., "DNA Hairpins: Fuel for Autonomous DNA Devices", Biophysical Journal, Oct. 2006, vol. 91, pp. 2966-2975.
Isaacs et al., "RNA synthetic biology", Nature Biotechnology, May 2006, vol. 24, No. 5, pp. 545-554.

(Continued)

*Primary Examiner* — Carolyn L. Smith
(74) *Attorney, Agent, or Firm* — Kauth, Pomeroy, Peck & Bailey LLP

(57) ABSTRACT

A catalytic system and method of catalyzing reactions that uses a novel toehold exchange mechanism that allows a specified input to catalyze the release of a specified output, which in turn can serve as a catalyst for other reactions is provided. This toehold exchange catalyst system, which can be driven forward by the configurational entropy of the released molecule, provides an amplifying circuit element that is simple, fast, modular, composable, and robust. Using this toehold exchange catalyst system it has been possible to construct and characterize several circuits that amplify nucleic acid signals, including a feed-forward cascade with quadratic kinetics and a positive feedback circuit with exponential growth kinetics.

37 Claims, 22 Drawing Sheets

OTHER PUBLICATIONS

Joyce, "Directed Evolution of Nucleic Acid Enzymes", Annu. Rev. Biochem, 2004, vol. 73, pp. 791-836.

Lederman et al., "Deoxyribozyme-Based Three-Input Logic Gates and Construction of a Molecular Full Adder", Biochemistry, 2006, vol. 45, pp. 1194-1199.

Levy et al., "Exponential growth by cross-catalytic cleavage of deoxyribozymogens", PNAS, May 27, 2003, vol. 100, No. 11, pp. 6416-6421.

Liu et al., "DNA-Templated Organic Synthesis: Nature's Strategy for Controlling Chemical Reactivity Applied to Synthetic Molecules", Agnew chem. Int., 2004, No. 41, pp. 4848-4870.

Macdonald et al., "Medium Scale Integration of Molecular Logic Gates in an Automaton", Nan Letters, 2006, vol. 6, No. 11, pp. 2598-2603.

Mao et al., "A nanomechanical device based on the B-Z transition of DNA", Nature, Jan. 14, 1999, vol. 397, pp. 144-146.

Marras et al., "Efficiencies of fluorescence resonance energy transfer and contact-mediated quenching in oligonucleotide probes", Nucleic Acids Research, 2002, vol. 30, No. 21, pp. 1-8.

Paul et al., "A self-replicating ligase ribozyme", PNAS, Oct. 11, 2002, vol. 99, No. 20, pp. 12733-12740.

Pei et al., "Behavior of Polycatalytic Assemblies in a Substrate-Displaying Matrix", J. Am. Chem. Soc., 2006, vol. 128, pp. 12693-12699.

Penchovsky et al., "Computational design and experimental validation of oligonucleotide-sensing allosteric ribozymes", Nature Biotechnology, Nov. 2005, vol. 23, No. 11, pp. 1423-1433.

SantaLucia, Jr., "A unified view of polymer, dumbbell, and oligonucleotide DNA nearest-neighbor thermodynamics", Proc. Natl. Acad. Sci., USA, Feb. 1998, vol. 95, pp. 1460-1465.

Seelig et al., "Catalyzed Relaxation of a Metastable DNA Fuel", J. Am. Chem. Soc., 2006, vol. 128, pp. 12211-12211.

Seelig et al., "Enzyme-Free Nucleic Acid Logic Circuits", Science, Dec. 8, 2006, vol. 314, pp. 1585-1588.

Seeman, "From genes to machines: DNA nanomechanical devices", Trends in Biochemical Sciences, vol. 30, No. 3, pp. 119-125, Mar. 2005.

Simmel et al., "A DNA-based molecular device switchable between three distinct mechanical states", Applied Physics Letters, Feb. 4, 2002, vol. 80, No. 5, pp. 883-885.

Stojanovic et al., "Deoxyribozyme-Based Ligase Logic Gates and Their Initial Circuits", J. Am. Chem. Soc., 2005, vol. 127, pp. 6914-6915.

Stojanovic et al., "Deoxyribozyme-Based Logic Gates", J. Am. Chem. Soc., 2002, vol. 124, pp. 3555-3561.

Tang et al., "Rational design of allosteric ribozymes", Chemistry & Biology, Jun. 1997, vol. 4., pp. 453-459.

Winfree et al., "Design and self-assembly of two-dimensional DNA crystals", Nature, Aug. 6, 1998, vol. 394, pp. 539-544.

Turberfield et al., "DNA Fuel for Free Running Nanomachines", Physical Review Letters, Mar. 21, 2003, vol. 90, No. 11, pp. 118102-1-118102-4.

Yurke et al., "A DNA-fuelled molecular machine made of DNA", Nature, Aug. 10, 2000, vol. 406, pp. 605-608.

Zuker, "Mfold web server for nucleic acid folding and hybridization prediction", Nucleic Acid Research, 2003, vol. 31, No. 13, pp. 3406-3415.

Isin et al., "Kinetics and Thermodynamics of Ligand Binding by Cytochrome P450 3A4", The Journal of Biological Chemistry, Apr. 7, 2006, vol. 281, No. 14, pp. 9127-9136.

International Search Report for International Application No. PCT/US2008/052959, Report completed Aug. 18, 2008, mailed Sep. 22, 2008, 3 pages.

* cited by examiner

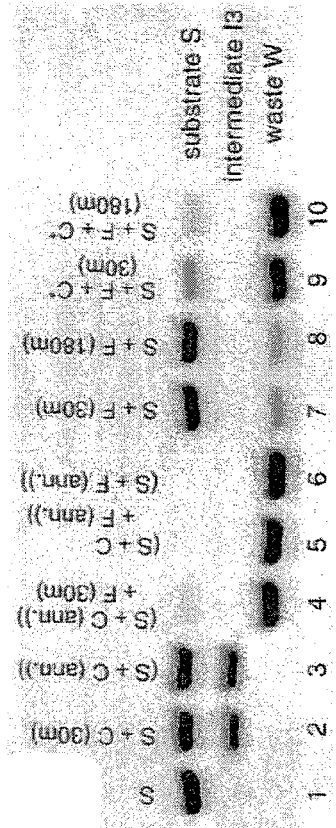
FIG. 5A
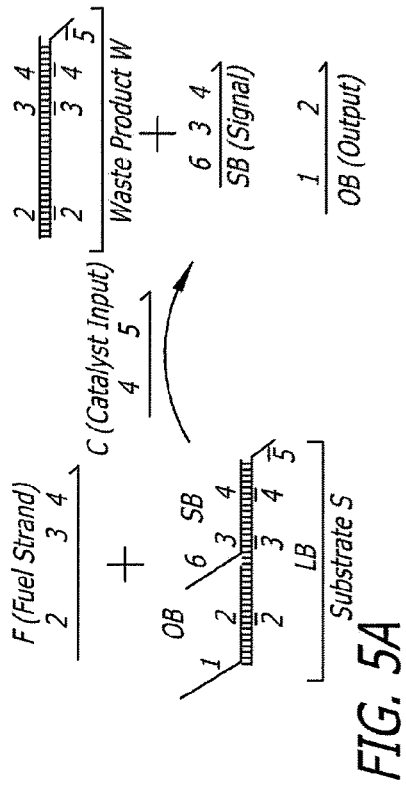
FIG. 5B
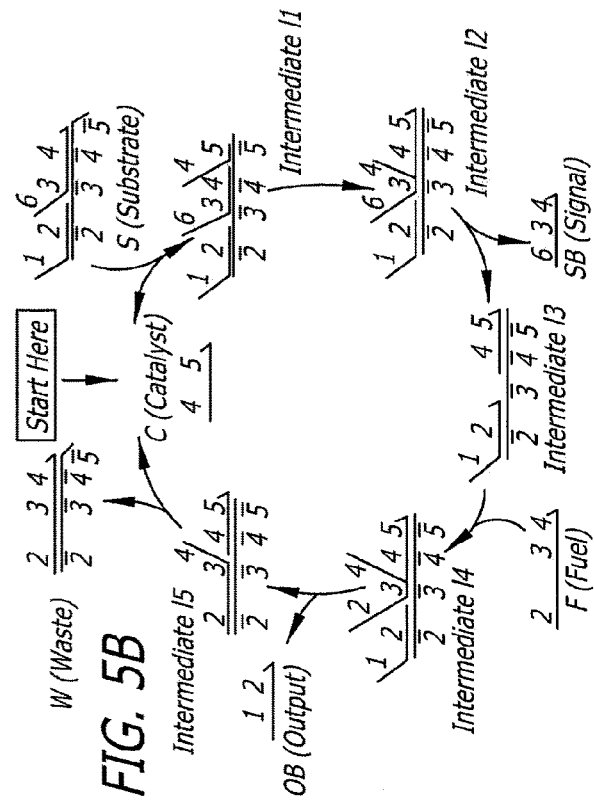
FIG. 5C
FIG. 5D

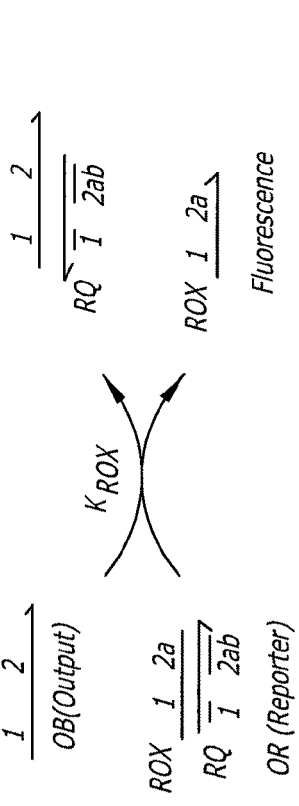
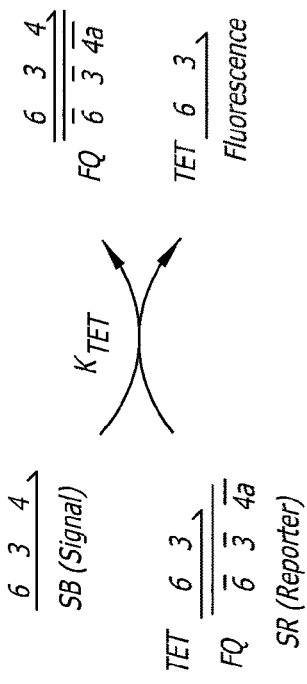
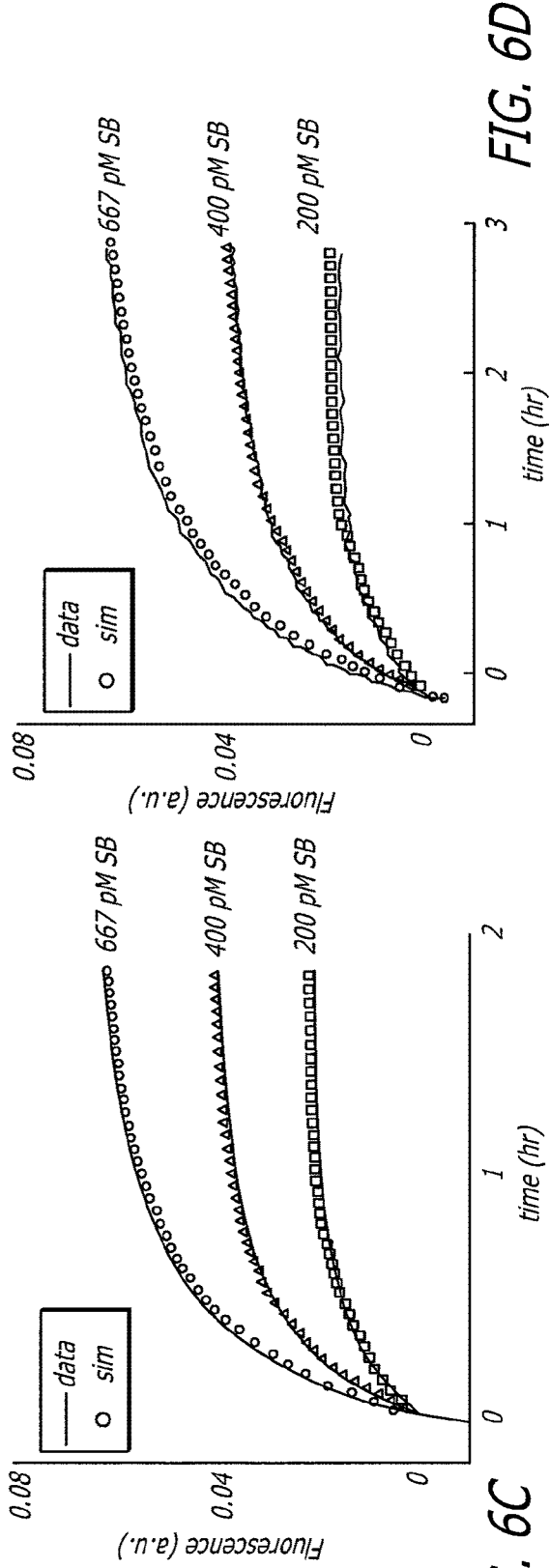

FIG. 10A
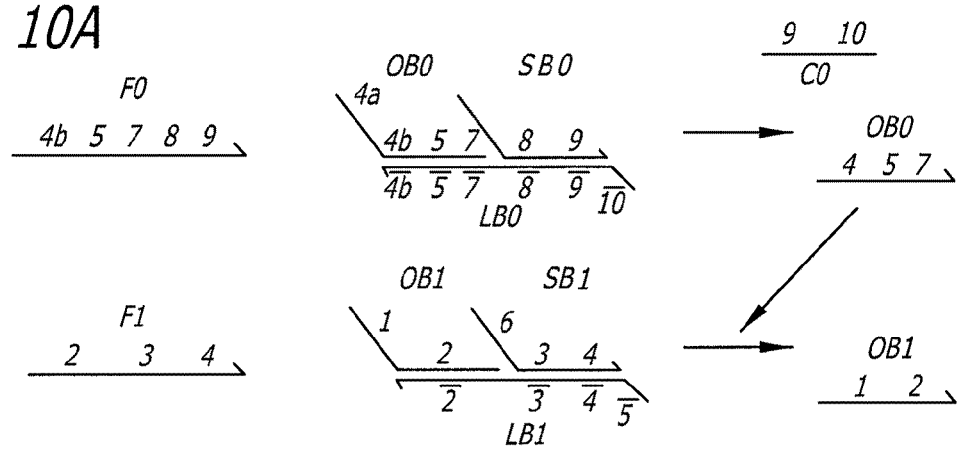
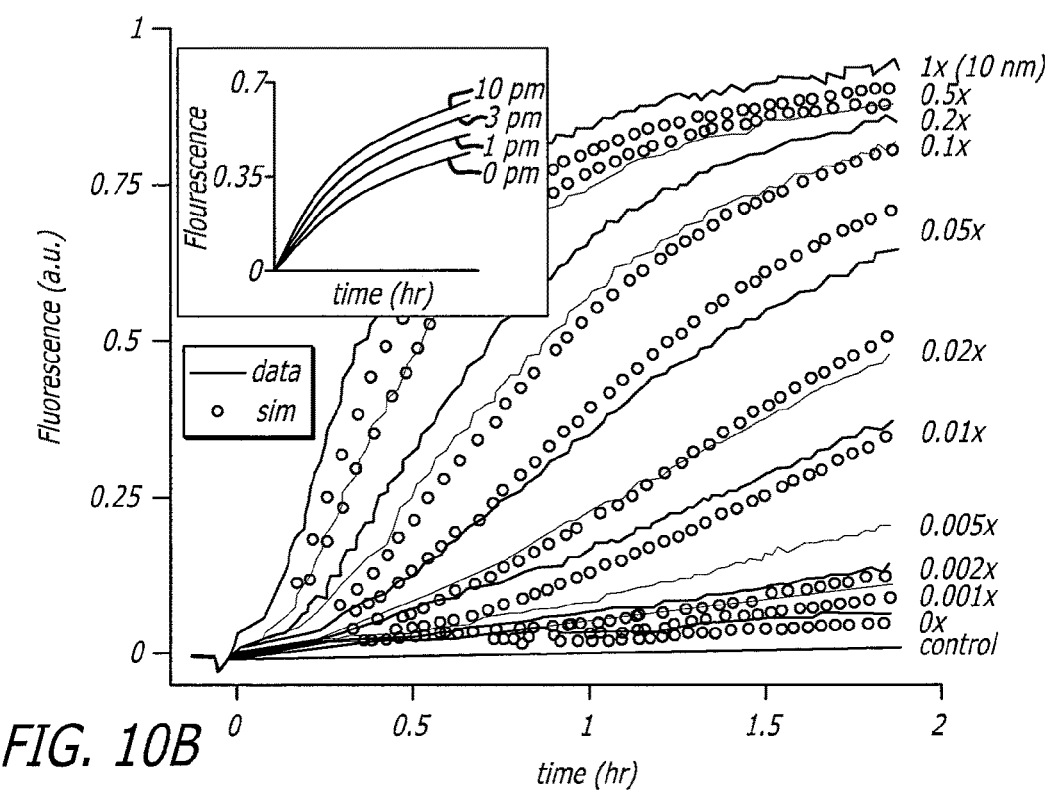
FIG. 10B

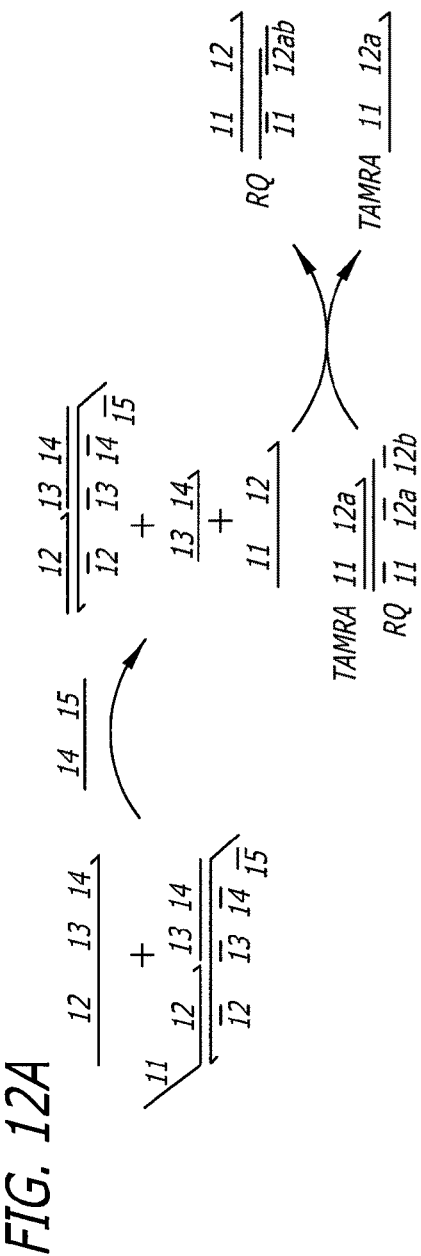
FIG. 12A
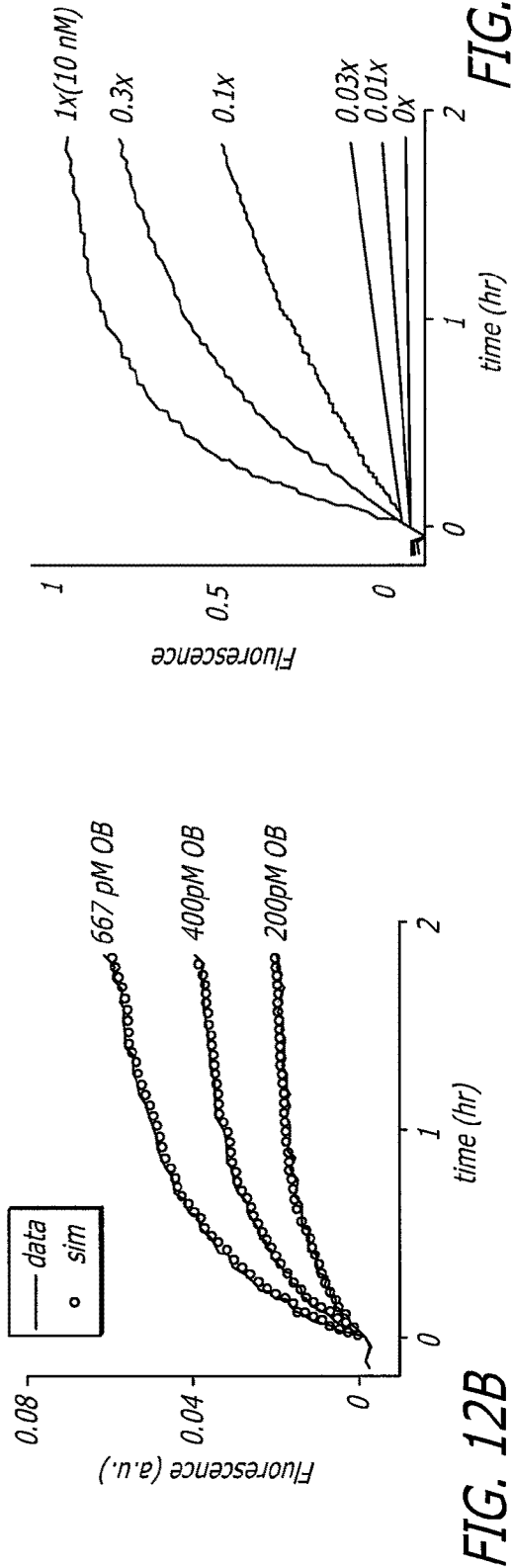
FIG. 12C
FIG. 12B

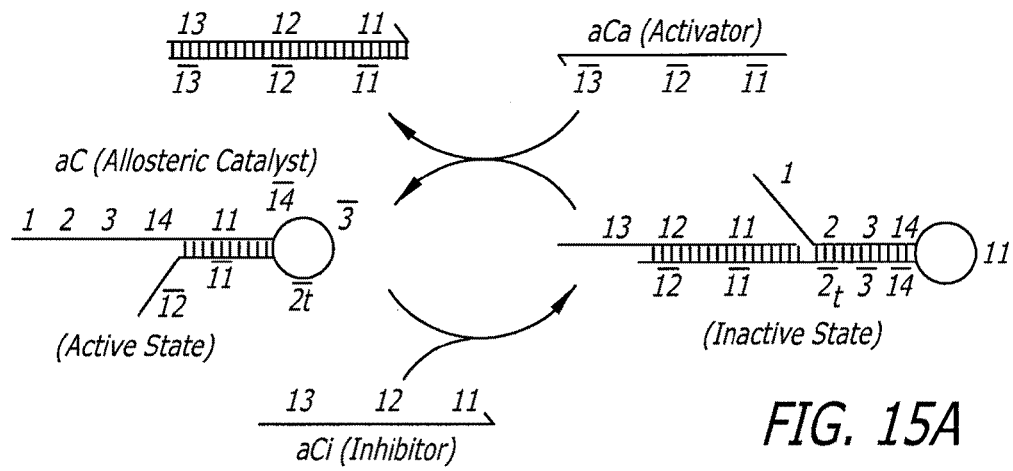
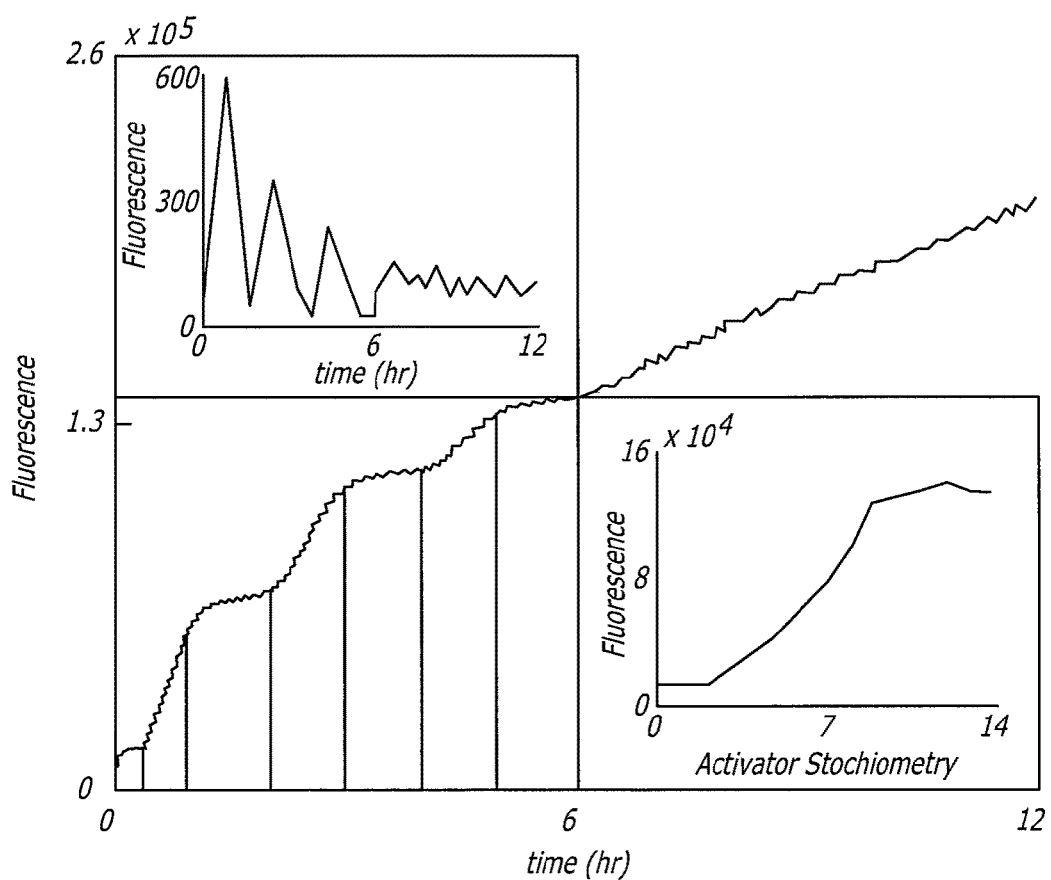
FIG. 15A
FIG. 15B

ENGINEERED TOEHOLD REACTIONS AND NETWORKS

CROSS-REFERENCE TO RELATED APPLICATIONS

The current application claims priority to U.S. Provisional Application No. 60/899,546, filed Feb. 5, 2007, the disclosure of which is incorporated herein by reference.

STATEMENT OF FEDERAL RIGHTS

The U.S. Government has certain rights in this invention pursuant to Grant No. DMS-0506468 awarded by the National Science Foundation.

FIELD OF THE INVENTION

The current invention is directed to a synthetic catalyst based on a toehold exchange phenomenon.

BACKGROUND OF THE INVENTION

Catalysts are molecules that speed up rates of target chemical reactions without being themselves consumed. Catalytic function is a necessary and ubiquitous component of life. Engineering catalysts may this allow for increased understanding of and control over biological systems. In nature, proteins are by far the most prevalent catalysts, but proteins are unfortunately difficult to engineer due to the complexity of its folding. (See, e.g., Hart W & Istrail S., Journal of Computational Biology, 4(1):1-22 (1997)) DNA, on the other hand, follows very specific Watson-Crick binding rules, and is a more suitable candidate. Additionally, many proteins denature fairly rapidly, while DNA possesses longer shelf-life. There are two basic ways of implementing DNA catalysts in the absence of proteins: to search the space of all DNA sequences to find catalytically active sequences of deoxyribozymes, and to engineer non-covalent catalysis using secondary structural properties of DNA. (See, e.g., Levy M & Ellington AD, PNAS 100(11), 6416-6421 (2003); Jaeger L, et al. PNAS, 96(26):14712-14717 (1999); and Lederman H, et al. Biochem., 45(4): 1194-1199 (2006), the disclosures of which are incorporated herein by reference.) Because it offers a more general solution (in terms of sequences), and also is more likely to function over a wider range of environmental conditions (temperature, salt, concentrations, etc.), the later is focused on in this disclosure.

In addition, nucleic acids are attractive because the combinatorial sequence space allows for an enormous diversity of signal carriers, and the predictability and specificity of Watson-Crick base pairing facilitate the design of gate architectures. The "RNA world" hypothesis further suggests that sophisticated biochemical organization can be achieved with nucleic acids alone (R. F. Gesteland, T. R. Cech, J. F. Atkins, Eds. The RNA World: The Nature of Modern RNA Suggests a Prebiotic RNA World (Cold Spring Harbor Laboratory Press, Cold Spring Harbor, N.Y., ed. 3, 2006) the disclosure of which is incorporated herein by reference), and nucleic acids have indeed been shown to be a versatile construction material for engineering molecular structures and devices (N. C. Seeman, Trends Biochem. Sci. 30, 119 (2005); and J. Bath & A. J. Turberfield, Nat. Nanotechnol. 2, 275 (2007) the disclosures of which are incorporated herein by reference), including catalytic (G. F. Joyce, Annu. Rev. Biochem. 73, 791 (2004); A. J. Turberfield et al., Phys. Rev. Lett. 90, 118102 (2003); and J. S. Bois et al., Nucleic Acids Res. 33, 4090 (2005); G. Seelig, B. Yurke, E. Winfree, J. Am. Chem. Soc. 128, 12211 (2006); and S. J. Green, D. Lubrich, A. J. Turberfield, Biophys. J. 91, 2966 (2006), the disclosures of which are incorporated herein by reference), and logical (M. N. Stojanovic, T. E. Mitchell, D. Stefanovic, J. Am. Chem. Soc. 124, 3555 (2002); M. N. Stojanovic, T. E. Mitchell, D. Stefanovic, J. Am. Chem. Soc. 124, 3555 (2002); J. Macdonald et al., Nano Lett. 6, 2598 (2006); H. Lederman, J. Macdonald, D. Stefanovic, M. N. Stojanovic, Biochemistry 45, 1194 (2006); and M. Hagiya, S. Yaegashi, K. Takahashi, in Nanotechnology: Science and Computation, J. Chen, N. Jonoska, G. Rozenberg, Eds. (Springer, New York, 2006), pp. 293-308, the disclosures of which are incorporated herein by reference) control elements and circuits (M. Levy, A. D. Ellington, Proc. Natl. Acad. Sci. U.S.A. 100, 6416 (2003); R. M. Dirks, N. A. Pierce, Proc. Natl. Acad. Sci. U.S.A. 101, 15275 (2004); M. N. Stojanovic et al., J. Am. Chem. Soc. 127, 6914 (2005); R. Penchovsky, R. R. Breaker, Nat. Biotechnol. 23, 1424 (2005); and G. Seelig, D. Soloveichik, D. Y. Zhang, E. Winfree, Science 314, 1585 (2006), the disclosures of which are incorporated herein by reference). Engineering (deoxy)ribozyme-based logic gates has been very effective, resulting in systems containing over 100 gates operating independently in parallel as well as systems demonstrating cascading of a signal between two gates. (See, Lederman H. Macdonald J, Stefanovic D, Stojanovic M N., Biochem 45(4): 1194-1199 (2006), the disclosure of which is incorporated herein by reference.) Alternatively, hybridization-based systems, usually driven by the energy of base-pair formation, have proven especially suitable for cascading signals, as demonstrated by a circuit five layers deep. (See, e.g., G. Seelig, et al., Science 314, 1585 (2006), the disclosure of which is incorporated herein by reference.) Finally, using DNA in vitro constructions of pure (non-deoxyribozyme) DNA systems also include logical circuitry (Seelig G, Soloveichik D, Zhang D Y, Winfree E." Science 314(5808): 1585-1588 (2006), the disclosure of which is incorporated herein by reference), nanomotors and nanomachines (C. Mao, W. Sun, Z. Shen, and N. C. Seeman, Nature 297, 144-146 (1999); Yurke B, Turberfeld A J, Mills A P, Simmel F C, Neumann J L., Nature 406, 605-608 (2000); and Simmel F C and Yurke B, Appl. Phys. Lett. 80: 883-885 (2002), the disclosures of which are incorporated herein by reference), and molecular macrostructures (Goodman RP, et al., Science 310, 1661-1665 (2005); and Winfree E, et al., Nature 394, 539-544 (1998), the disclosures of which are incorporated herein by reference), as well as catalytic systems have been developed. (Turberfeld A J, et al., Phys Rev Lett 90, pp 118102.11 14; Dirks R M and Pierce N A, PNAS, 101(43): 15275-15278, 2004; and Seelig G, Yurke B, Winfree E., JACS 128(37): 12211-12220 (2006), the disclosures of which are incorporated herein by reference.)

These artificial biochemical circuits are likely to play as large a role in biological engineering as electrical circuits have played in the engineering of electromechanical devices. Toward that end, nucleic acids provide a designable substrate for the regulation of biochemical reactions. However, it has been difficult to incorporate signal amplification components.

The development of modular biochemical circuit elements poses several challenges. First, distinct signals must be carried by distinct chemical species, motivating the use of information-carrying molecules whose sequences can be used to encode signal identity. Second, "wiring up" a gate to specified inputs and outputs involves the design and synthesis of new molecules; this calls for modular gate designs. Third, a fast and robust catalytic mechanism must be identified and coupled to a suitable energy source in order to create gates with signal gain. Fourth, it must be possible to construct circuits of arbitrary complexity that can produce an unlimited variety of dynamical behaviors. Finally, there should be no leak or crosstalk between distinct signals and gates. It is difficult to meet all these challenges simultaneously. Accordingly, to date no system has been developed that would allow a rapid toehold catalysis system to be developed. Accordingly, a need exist for an improved DNA catalysis system for use in creating DNA networks.

SUMMARY OF THE INVENTION

The current invention is directed to a mechanism and system for catalyzing molecular equilibrium, using a novel catalyst design principle known as toehold exchange. In such a system, the equilibrium of a chemical reaction can be engineered to strongly favor the products by using configurational entropy as a driving force.

In one embodiment, the catalyst is cascaded into two-layer feed-forward and feedback networks, allowing access to quadratic and exponential kinetics.

In another embodiment, an allosteric version of the catalyst is presented, which can be dynamically switched between two states.

In still another embodiment, catalytic Boolean AND/OR gates are implemented and demonstrated using a variation of the catalyst design. In such an embodiment it is shown that by combining the logical AND gate with the autocatalyst, a super-exponential amplifier can be obtained.

In yet another embodiment, the catalyst system provided for use in a number of applications, such as, for example, in situ and in vivo biological detection, quantitative analysis and control.

BRIEF DESCRIPTION OF THE FIGURES

Various examples of the present invention will be discussed with reference to the appended drawings, wherein:

FIGS. 5a to 5e show schematics of the mechanism and test results for a exemplary toehold DNA catalyst in accordance with one embodiment of the current invention;

FIGS. 6a to 6d show schematics of the mechanism and test results for a reporter scheme for a exemplary toehold DNA catalyst in accordance with one embodiment of the current invention;

FIGS. 10a and 10b show schematics of the mechanism and test results for an exemplary two-layer cascaded network formed using the toehold DNA catalyst in FIG. 5;

FIGS. 12a to 12c show schematics of the mechanism and test results for an exemplary independent input/output catalyst system formed using the toehold DNA catalyst in FIG. 5;

FIGS. 15a to 15c show schematics of the mechanism and test results for an exemplary allosteric catalyst circuit formed using the toehold DNA catalyst in accordance with one embodiment of the current invention;

These drawings depict only illustrative examples of the invention and are not to be considered limiting of its scope

DETAILED DESCRIPTION OF THE INVENTION

The current invention is directed to a catalytic design strategy that uses a novel toehold exchange mechanism that allows a specified input to catalyze the release of a specified output, which in turn can serve as a catalyst for other reactions. This reaction, which can be kinetically driven forward by the configurational entropy of the released molecule, provides an amplifying circuit element that is simple, fast, modular, composable, and robust. Using this system it has been possible to construct and characterize several circuits that amplify nucleic acid signals, including a feed-forward cascade with quadratic kinetics and a positive feedback circuit with exponential growth kinetics.

Catalytic activity has two characteristic behaviors: the speedup of the target reaction and the re-release of the catalyst to allow for multiple turnovers. To achieve these behaviors, the novel design principle of toehold exchange is used in the current invention (see, FIGS. 1 to 4). This "toehold exchange" process integrates many of the concepts of traditional DNA catalyst systems with a novel secondary-structure based catalyst system in which a small "toehold" site on a molecule, such as a domain on a single-stranded DNA (henceforth "strand"), catalyzes the release of a molecule or strand of similar length but independent sequence from a multistranded complex.

Figure 1:
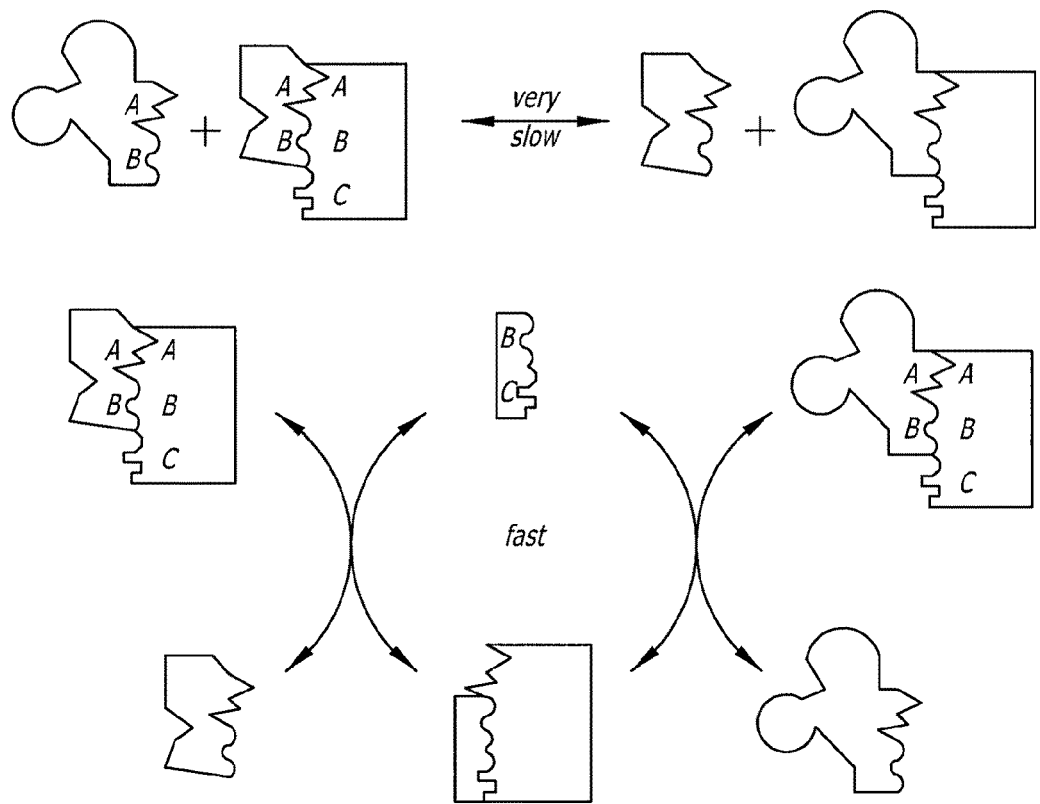
FIG. 1 provides schematics of the basic operation of an exemplary embodiment of the toehold catalyst system in accordance with the current invention.

As shown in FIG. 1, the basic operation of the catalyst system of the current invention involves the usage of partial-binding molecules, i.e., molecules having "toehold" binding sites to catalyze ligand-exchange. In this system two different ligands exist with coordinating left-hand side (LHS) functional groups (A & B). One starts bound to a substrate molecule, expressing the right-hand side (RHS) functional groups (A, B & C). Exchange between these two ligands would be exceedingly slow if the thermodynamics of binding were strong as shown in the top schematic of FIG. 1. Accordingly, in order to catalyze the exchange, the current system uses a catalyst molecule having a "toehold" site, which in the schematic in FIG. 1 is the RHS functional group C when the substrate molecule is bound to the AB molecule. "Toehold exchange" refers to the fact that the substrate molecule initially expresses an exposed toehold functional group C, but later expresses functional group A when the catalyst binds the substrate. This functional group B then allows the other ligand molecule expressing A and B to bind to the substrate. Since the catalyst molecule can displace and be displaced by both of the ligands expressing LHS (A & B) functional groups, it increases the rate at which the two ligands reach equilibrium.

Figure 2:
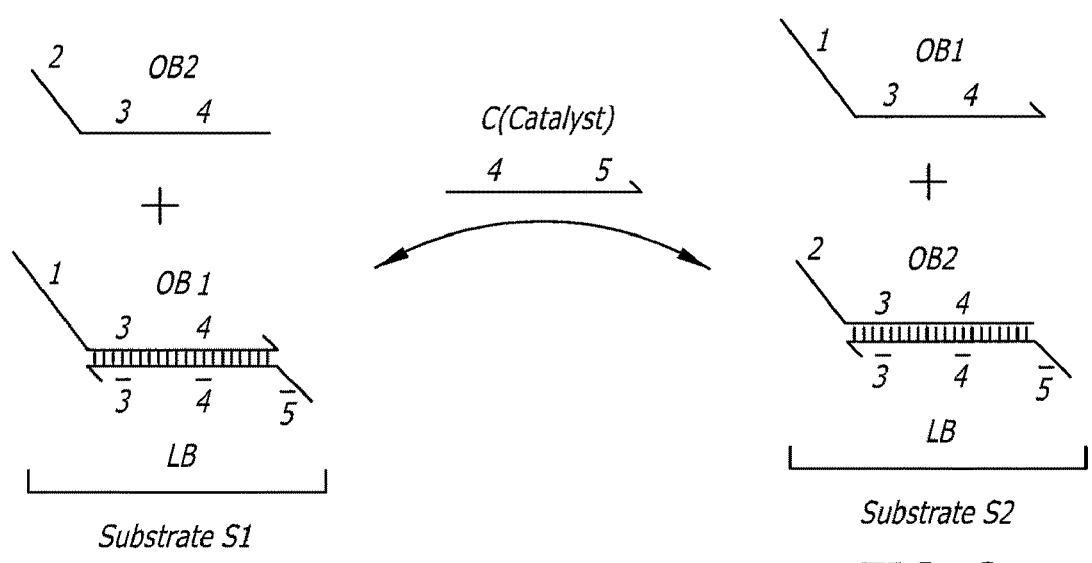
FIG. 2 provides a schematic of an example of the application of the toehold catalyst of the current invention to DNA reactions.
Figure 3:
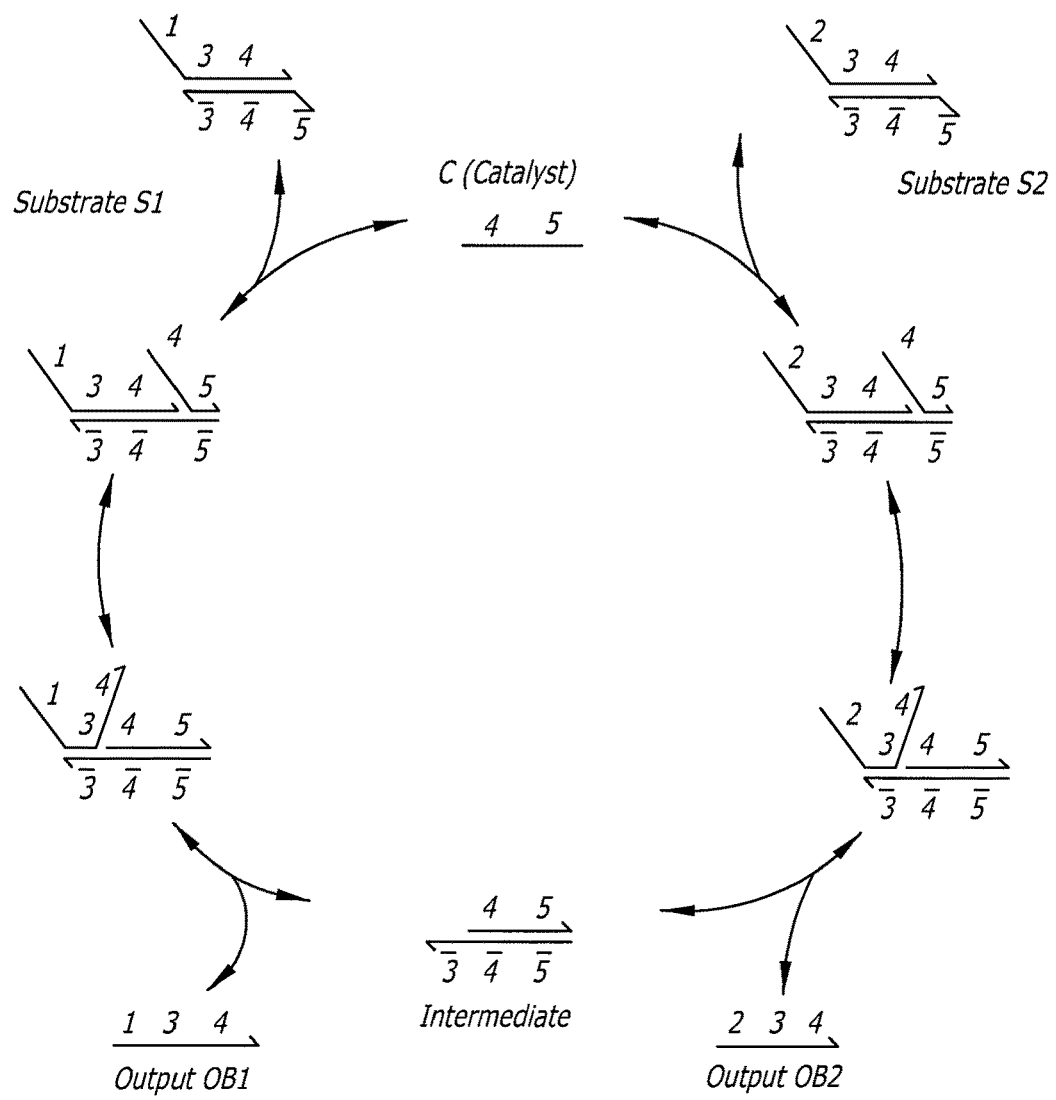
FIG. 3 provides a schematic of an example of the application of the toehold catalyst of the current invention to DNA reactions.
Figure 4:
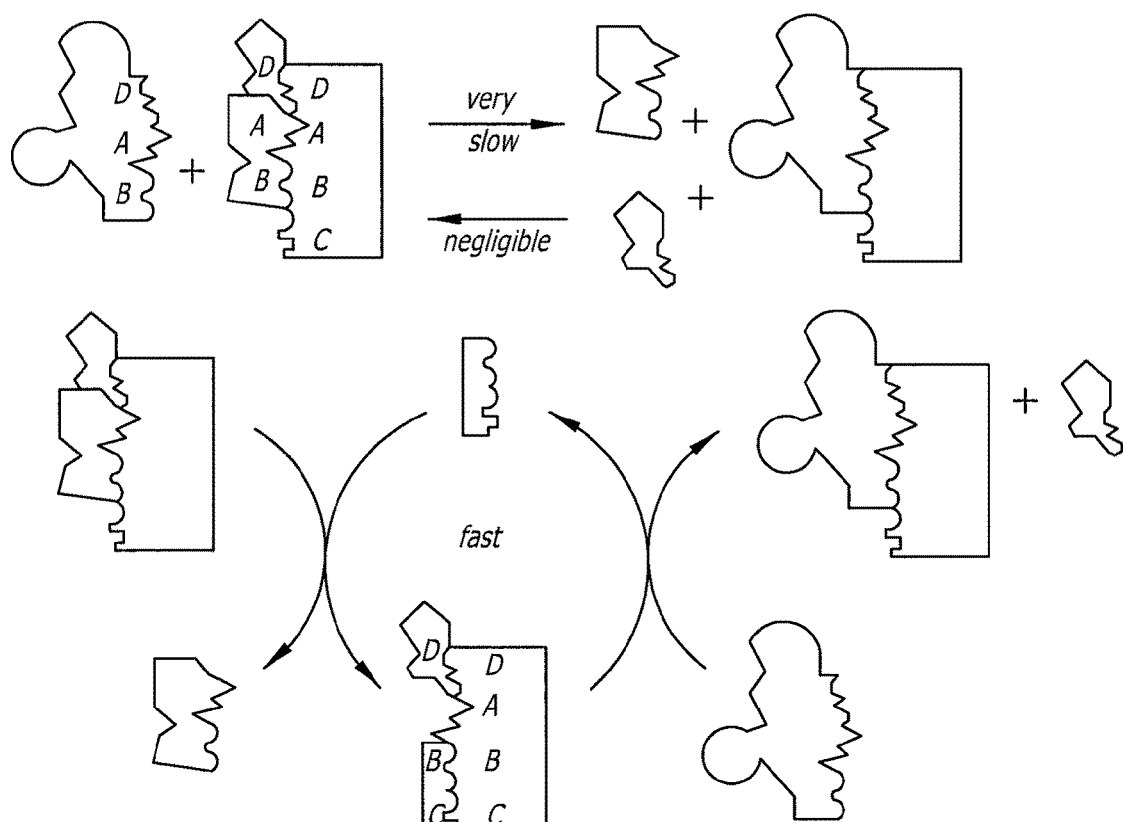
FIG. 4 provides schematics of another exemplary embodiment of the toehold catalyst system in accordance with the current invention.

As an example, FIGS. 2 and 3 provide schematics of the operation of this entropy drive catalyst system in operation with DNA. In these figures the OB1 strand and the OB2 strand serve as the two ligands that both can bind to substrate DNA strand LB. The two ligands, in the absence of catalyst strand (C), exchange with each other in binding to the substrate molecule only very slowly (see FIG. 2). However, in the presence of small amounts of the toehold catalyst of the current invention this exchange is sped up through well-understood branch-migration kinetics (as shown schematically in FIG. 3).

Moreover, unlike previous synthetic chemical systems, the primary driving force of the catalyzed reaction can be entropy, which is a commonly-used powering mechanism of biological systems. Specifically, the reactions of the current invention may be driven using the configurational entropy gain of additional liberated molecules. For example, in regard to the schematic shown and discussed in FIG. 1 above, in order to favor the binding/release of one binding over another, the specific binding region of favored ligand is expanded to include the full binding region of another ligand. This is represented schematically in FIG. 4 by the small molecule displaying the LHS functional group (D). Modified in this way, the reverse reactions in the catalytic processes become negligible, and the reaction is driven in one direction. Other natural examples of this phenomenon can be found in nature, such as, for example, ATP, which also relies heavily on entropy as driving force.

The fundamental reaction mechanism presented here, based on branch migration and driven by entropy, differs from the traditional view of catalysis in biological organisms in that it requires no enzymes and alters no covalent bonds. However, it is capable of molecular state changes and control, just as orthodox chemistry involving covalent bonds It is important to ensure that alternative interactions do not interfere with intended gate functions. Toward this end, a key design principle is that the complements of the ligand domains never appear in their single-stranded form. This concept, in principle, functions for any chemistry exhibiting specific non-covalent binding between functional groups, from small polar organic molecules to polypeptides joined in quaternary structure by sterics and electrostatic.

Because the toehold catalytic mechanism of the current invention is entirely artificially engineered and a number of experimental examples using the catalyst system are provided herein. For example, using the toehold catalyst system of the current invention it is possible to cascade different systems of DNA catalysts, demonstrating the robustness of the catalyst to larger networks. It is also possible to develop catalyst networks that provide exponential kinetics by modifying the catalyst to be an autocatalyst, further showing that feedback can be achieved with catalysis. Next, an allosteric catalyst capable of dynamically switching states is demonstrated that is capable of catalyzing one of two different reactions depending on its state, thereby showing that nanomachines can serve as a control mechanism for catalysis. Finally, the current invention also demonstrates the possibility of constructing catalytic Boolean logic gates, wherein the production rate of output depends on the logical behavior of its inputs, thus integrating catalysis with logic.

As a result of the robustness and versatility of the toehold catalyst of the current invention a wide variety of potential applications are available, including, for example, in vivo detection, quantitative analysis, and control mechanisms. A number of exemplary applications, networks and circuits are described in the examples below.

EXAMPLES

The following technical specifications were used in the examples presented below.

DNA Sequence Design

The DNA sequence design process was done on a domain level. Domains denoted by unmodified numbers are termed primary domains, while domains denoted by barred numbers are termed complementary domains. First, random sequences composed of only A, C, and T were generated for each of the primary domains. Since in the intended reaction pathway only primary domains ever are exposed as single-stranded regions, this choice reduces potential secondary structure. (See, e.g., K. U. Mir, Proc. DNA Based Computers II 44, 243 (1999), the disclosure of which is incorporated herein by reference.) Sequences for complementary specificity domains were constructed accordingly. Next, subsequences known to be problematic (4 or more G's in a row on complementary domains due to G-quadruplexing, more than 4 A's in a row causing synthesis difficulties, etc.) were altered by hand. The remaining sequences were then concatenated as appropriate to form the DNA strands. These were folded alone and pairwise using the mFold web-server to determine possible spurious bindings. (See, M. Zuker, Nucleic Acids Res. 31, 3406 (2003), the disclosure of which is incorporated herein by reference.) Some bases at problematic subsequences were then changed by hand to G in the primary domains (and propagated elsewhere as appropriate for domain identity), to minimize self-folding and pairwise-folding energies. Finally, the strands were checked again on mFold to ensure minimal spurious interactions. Although only artificial nucleotide sequences are discussed above, it should be understood that the current catalyst construction mechanism is also expected to work for generalized sequences, though the kinetics of reactions involving nucleic acids with high secondary structure may be significantly slower. In a case where naturally occurring DNA and RNA sequences are used these sequences will typically incorporate all four nucleotides.

Substrate Purification

Substrate and reporter complexes were manually purified to ensure proper stochiometry and to improve purity. Sources of substrate impurity include synthesis errors and truncations, partially-formed complexes due to imperfect stochiometry, and dimerization. Strands for each sample were prepared with nominally correct stochiometry at 20 μM and annealed. For all substrate complexes except the autocatalyst substrate, the fuel strand was then added, which triggers many poorly formed substrates to decay into products that can be removed by gel purification. (For the autocatalyst, addition of the fuel strand would have initiated the exponential chain reaction, so the autocatalyst substrate was purified without addition of the fuel strand.) The samples were then run on 12% non-denaturing polyacrylamide gel electrophoresis (PAGE) gel at 180V for 6 hours. The proper bands were cut out and eluted in TE/Mg2+ buffer for 2 days. Typical prep sizes ranged from 5 nmol to 10 nmol, and typical elution volume was 2 ml. Typical yields ranged from 40% to 60%. Purified complexes were quantified by measurement of absorbance at 260 nm, using extinction coefficients for single- and double-stranded DNA predicted by nearest-neighbor models. (See, M. Zuker, Nucleic Acids Res. 31, 3406 (2003), the disclosure of which is incorporated herein by reference.)

All annealing processes were performed with an Eppendorf Mastercycler Gradient thermocycler. The samples were brought down from 95° C. to 20° C. at a constant rate over the course of 90 minutes.

DNA Oligonucleotides

DNA oligonucleotides used in this study were purchased from Integrated DNA Technologies (IDT), with HPLC purification. Where applicable, fluorophores were attached by IDT as well.

Buffer Conditions

The buffer for all experiments was TE (10 mM Tris HCl pH balanced to 8.0, 1 mM EDTA), purchased in 100× stock from Sigma-Aldrich (catalog number T9285), with 12.5 mM $MgCl_2$ added.

Gel Electrophoresis

Non-denaturing PAGE was run on 12% acrylamide (19:1 acrylamide:bis), diluted from 40% acrylamide stock purchased from Ambion (catalog number AM9022). ND loading dye-containing XCFF in 50% glycerol was added in 0.2× stochiometry to all samples. Gels were run at 25° C. using a Novex chamber with external temperature bath. Gels were stained with Sybr-Gold stain, purchased from Invitrogen (catalog number S-11494), and scanned with a Bio-Rad Molecular Imager. Formation gels shown in the figures were run at 180V for 1 hour.

Total RNA and Cell Lysate.

In the experiment described in FIGS. 18 & 19, inset 2, below mouse liver total RNA and active rabbit reticulocyte lysate were used. They were both purchased from Ambion (catalog numbers AM7810 and AM1200), as part of their in vitro translation kit. The lysate included exogeneously introduced RNAse inhibitor enzymes; it is not expected that this significantly affect the results of the experiment described.

Spectrofluorimetry Studies

Spectrofluorimetry studies were done with a commercial SPEX Fluorolog-3 from Horiba. Cuvettes used were 119-004F synthetic quartz cells purchased from Hellma, with total volume 1.6 ml. For studies observing behavior of the TET fluorophore, excitation was at 524 nm, while emissions was at 541 nm. For studies observing behavior of the ROX fluorophore, excitation was at 588 nm, while emissions was at 602 nm. For studies observing behavior of the TAMRA fluorophore, excitation was at 557 nm, while emissions was at 580 nm. Slit size used was 2 nm for both excitation and emission monochromoters for net reaction studies, and 3 nm for individual rate measurements. All experiments were done with integration time of 3 seconds for every 30 second time-point. Prior to each experiment, all cuvettes were cleaned thoroughly: each cuvette was washed 15 times in distilled water, once in 70% ethanol, another 5 times in distilled water, and finally once more in 70% ethanol.

Fluorescence Normalization

All fluorescence experiments show fluorescence values normalized to approximately 1 a.u.=10 nM. Simulation traces (dotted lines) are offset vertically to correspond to quenched fluorophore baselines. Data traces within a single figure are normalized using the same scaling factor, which was determined by best-fit to simulation traces. Data traces across different figures possess different scaling factors due to differences in fluorescence reporter, lamp luminosity, and substrate concentrations. Time t=0 signals the beginning of the reaction, triggered by the addition of the last necessary reagent (usually the substrate).

Inactivity of Carrier Strands

In the course of testing the catalyst system and its derivatives, some reactions required very small quantities of certain DNA species. For example, in FIG. 12b (inset), 1 pM of C0 in 1.5 ml of solution=1.5 fmol of DNA. It has been observed that DNA sticks non-specifically to pipette tips, so that direct serial dilutions lead to stocks much more dilute than expected. To address potential tip loss a non-reactive 20 nt poly-T "carrier" strand was introduced into all dilute stocks (1 µM and below) at a concentration of 1 µM. Since pipette tip loss is non-specific, the majority of DNA loss would be of the carrier strand, so that serially diluted stocks are only slightly more dilute than expected. It is of interest to verify that the carrier strand does not affect kinetics. Thus, the performance of the catalyst at concentration ranges where pipette loss is not substantial were compared against these dilute stock solutions. It was determined that the presence of the carrier strand has very little, if any, effect on the kinetics of the catalyst, at 100× excess.

Example 1

Generic Toehold Exchange Catalytic Gates

An example is provided to show the basic implementation of the synthetic toehold exchange DNA catalyst. Although not required by the underlying invention, the design presented in the example shows a model catalyst system wherein a small single-stranded nucleic acid molecule catalytically releases another small single-stranded nucleic acid molecule of independent sequence from a multi-stranded complex by the process of toehold exchange. In addition, the catalyst system shows a synthetic reaction that is driven primarily by the entropy gain of molecules released, and not by the energetics of bond formation, either covalent or non-covalent.

As explained above, the toehold catalytic gate presented herein is substantially simpler than previous hybridization-based designs; moreover, it is faster, better understood, and more modular. An exemplary reaction is shown in FIG. 5A. In this example, fuel strand (F) reacts with the three-stranded substrate complex (S), displacing output and signal strands (OB and SB) from linker strand (LB) to form waste complex (W). As further shown, the total number of base pairs in the reactants and products is unchanged; the reaction is driven forward thermodynamically by the entropic gain of the liberated molecules. Fuel, signal, catalyst, and output are all single-stranded DNA molecules that can be of similar lengths; thus, each molecule may play multiple roles within a network. For example, the output of one gate may serve as the input to another. Notably, catalyst C and output OB may be entirely independent in sequence; this modularity implies that a catalytic gate can be designed to act at any point within a preexisting circuit. [Note: In the system presented in FIG. 5, there is some sequence redundancy in the domain sequences chosen (for example, 2b and 5 are identical).] This is because all four systems presented were designed together, with the goal of minimizing the number of differences between systems. In the design of a catalytic reaction in isolation, there are no sequence constraints; as will be discussed in detail below a system with completely independent catalyst and output but with very similar kinetics to that of the reaction shown in FIG. 5 is provided in FIG. 15.

As previously discussed, unlike previous hybridization-based catalyst systems, the reaction design does not require unusual secondary structures such as pseudoknots and kissing loops. Moreover, undesired interactions can be avoided by design, resulting in reliable and predictable circuit behavior. (See, e.g., M. Zuker, Nucleic Acids Res. 31, 3406 (2003); J. Sager, D. Stefanovic, in DNA Computing: 11th International Workshop on DNA Computing, A. Carbone, N. A. Pierce, Eds. (Springer, Berlin, 2006), pp. 275-290; and K. U. Mir, in DNA-Based Computers II: DIMACS Workshop, L. F. Landweber, E. B. Baum, Eds. (American Mathematical Society, Providence, R.I., 1999), pp. 243-246, the disclosures of which are incorporated herein by reference.) Strands are conceptually subdivided into functional domains (number labels in FIG. 5) whose sequences determine the pattern of interactions between circuit components. Some exemplary domain sequences are given in Table 1, below. The domains can be conceptually grouped by purpose: domains 3 and 5 are termed toehold domains, whereas domains 1, 2, 4, and 6 are termed specificity domains.

TABLE 1

Exemplary Domain Sequences of Basic Catalytic Reaction

| Domain | Sequence | Length (nt) |
|---|---|---|
| 1 | 5'-CTTTCCTACA-3' (SEQ ID 1) | 10 |
| 2a | 5'-CCTACG-3' | 6 |
| 2b | 5'-TCTCCA-3' | 6 |
| 2c | 5'-ACTAACTTACGG-3' (SEQ ID 2) | 12 |
| 3 | 5'-CCCT-3' | 4 |
| 4 | 5'-CATTCAATACCCTACG-3' (SEQ ID 3) | 16 |
| 5 | 5'-TCTCCA-3' | 6 |
| 6 | 5'-CCACATACATCATATT-3' (SEQ ID 4) | 16 |

In general, toehold domains are short enough to bind only fleetingly in the absence of additional binding (and need not be distinct), but they greatly accelerate the initiation of strand displacement reactions. (See, B. Yurke, A. P. Mills, Genet. Program. Evolvable Mach. 4, 111 (2003), the disclosure of which is incorporated herein by reference.) Specificity domains, meanwhile, ensure specific interactions [even a single mismatch can slow down branch migration substantially (I. G. Panyutin, P. Hsieh, J. Mol. Biol. 230, 413 (1993), the disclosure of which is incorporated herein by reference) and determine the identities of the catalyst and output molecules. The lengths of the toehold domains determine kinetics and need to be between roughly 4 and 10 nucleotides (nt), but the specificity domains may be of any length sufficient to ensure thermal stability. Domains 1 and 6 of OB and SB, respectively, are inert, whereas their respective toeholds are sequestered in S.

In the toehold exchange reaction of the current example, as shown in FIG. 5*b*, C first binds to the single-stranded toehold domain $\overline{5}$ on S to form the four-stranded intermediate I1, which then rearranges (by branch migration) to form I2. The binding between toehold domains 3 and $\overline{3}$ is too weak to keep SB attached, so I2 spontaneously dissociates into SB and I3. Newly exposed $\overline{3}$ then facilitates the binding of F, resulting in I4, which then quickly rearranges to release OB and I5. Finally, I5 rearranges so that C is attached only by the binding of 5 and $\overline{5}$, which spontaneously dissociates to leave W and regenerate C. As discussed above, to ensure that alternative interactions do not interfere with intended gate functions except at toeholds, no two molecules interact with each other via complementary single-stranded domains. The catalytic design is therefore expected to function for most choices of domain sequences lacking strong secondary structure and spurious mutual interactions.

In FIG. 5*c*, polyacrylamide gel electrophoresis (PAGE) is used to verify the catalytic pathway. By reacting substrate S (purified by gel) and catalyst C in the absence of fuel F, it is possible to prevent the reaction from progressing past intermediate I3. As shown, the amount of I3 produced after 30 min (lane 2) is almost identical to that present at equilibrium, as assessed by annealing the reaction components (lane 3). This suggests that all reactions up to I3 are fast on this time scale. Similarly, the subsequent reaction between I3 and F is also fast (lanes 3 to 5). The complete system behaves as expected: The uncatalyzed reaction is slow (lanes 7 and 8), and a sub-stochiometric quantity (0.1×) of C enables the reaction to proceed rapidly to near-completion (lanes 9 and 10). In order to measure the time course of the catalyzed reaction by means of a fluorescent reporter without interference from fluorophore-quencher interactions, an indirect reporter complex OR is used. (See, S. A. Marras, F. R. Kramer, S. Tyagi, Nucleic Acids Res. 30, e122 (2002), the disclosure of which is incorporated herein by reference.)

The kinetics of the model system were monitored using independent reporter complexes OR and SR. This approach was chosen (rather than direct labeling of strands in the catalyst system) to decouple the thermodynamic effects of fluorophore-quencher binding from the catalytic pathway. Both OR and SR initially contain a 20 bp duplex and a 7 nt toehold domain that uniquely binds their respective targets (OB and SB). Each possesses a different fluorophore and quencher pair (TET and Iowa Black Fluorescence Quencher (FQ) for SR; ROX and Iowa Black Red Quencher (RQ) for OR). The reactions are assumed to be non-reversible, as given by the reaction schematics below:

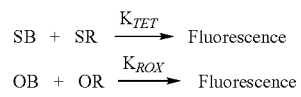

$$SB + SR \xrightarrow{K_{TET}} \text{Fluorescence}$$
$$OB + OR \xrightarrow{K_{ROX}} \text{Fluorescence}$$

Displacement rate constants of the two reporter complexes OR and SR were measured via fluorescence at initial reactant concentrations of 1 nM (1/30 the concentration used in catalyst experiments) to be $k_{TET}=8 \cdot 10^5$ M$^{-1}$s$^{-1}$ and $k_{ROX}=4 \cdot 10^5$ M$^{-1}$s$^{-1}$, as shown in FIGS. 6*a* to 6*d*. Specifically, FIG. 6*a* shows a schematic of signal (SB) reporter using TET and Iowa Black Fluorescence Quencher (FQ), and FIG. 6*b* shows a schematic of output (OB) reporter using ROX and Iowa Black Red Quencher (RQ). FIG. 6*c* shows data for the displacement rate of strand SF by SB at 25° C. Reporter complex SR was present in solution at 1 nM at t≈0, and various amounts of SB were added at t≈0. Dotted lines show simulation traces of a second-order displacement reaction with rate constant $k_{TET}=8 \cdot 10^5$ M$^{-1}$s$^{-1}$. Finally, FIG. 6*d* shows data for the displacement rate of strand OF by OB at 25° C. In this study reporter complex OR was present in solution at 1 nM at t≈0, and various amounts of OB were added at t≈0. Again dotted lines show simulation traces of a second-order displacement reaction with rate constant and $k_{ROX}=4 \cdot 10^5 M^{-1}s^{-1}$. The observed difference in displacement rate constants may be due to either the thermodynamics of the fluorophore/quencher pairs, differences in binding strength of the toehold domains, or secondary structure differences in SB and OB.

Figure 5E:
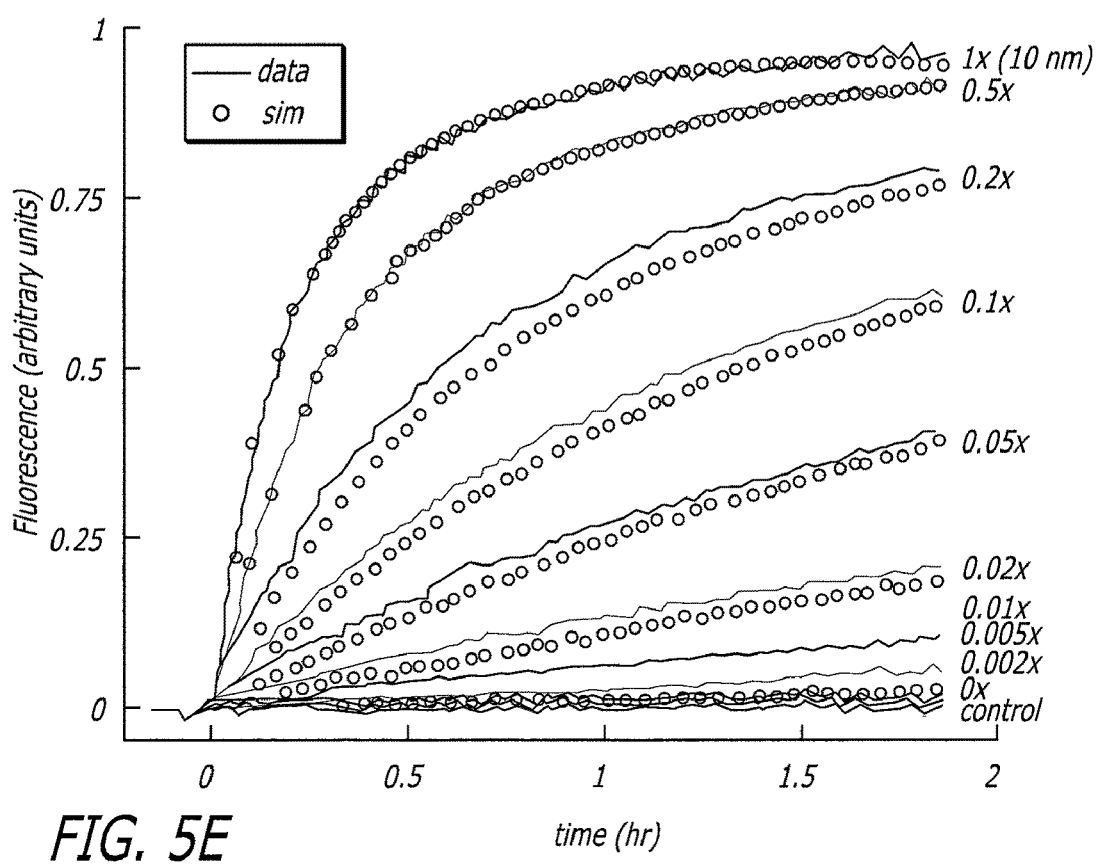

During the operation of these reporter, OR reacts stochiometrically with output OB to separate a fluorophore-labeled strand from a quencher-labeled strand, thereby increasing fluorescence (FIG. 5D). The rate constant for the reporter system was measured to be $k_{ROX}=4 \cdot 10^5\ M^{-1}s^{-1}$. Because initial [OR]=30 nM is in excess to [S]=10 nM, the reporter complex remains substantially in excess, and the reporting delay should remain less than 100 s, which is short as compared to the half time of the catalyzed reactions. OR does not react substantially with S, because there are no single-stranded toeholds to initiate interaction. Measurements of the kinetics of the catalyzed reaction over a 500-fold range of catalyst concentration are shown in FIG. 5E.

This system was modeled using the reduced reaction set shown in the reaction schematic below.

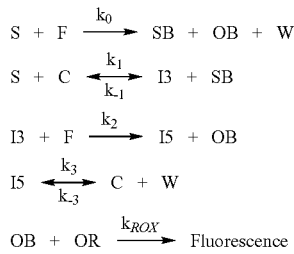

where $k_0=2.3 \cdot 10^1\ M^{-1}s^{-1}$, $k_1=6.5 \cdot 10^5\ M^{-1}s^{-1}$, $k_2=4.2 \cdot 10^5\ M^{-1}s^{-1}$, $k_3=4 \cdot 10^{-3}\ s^{-1}$ (fitted), and $k_{ROX}=4 \cdot 10^5\ M^{-1}s^{-1}$. The first reaction shown models an uncatalyzed (leak) reaction. Intermediate steps in branch-migration reactions are omitted, because they are relatively fast at experimental concentrations (C. Green, C. Tibbetts, Nucleic Acids Res. 9, 1905 (1981), the disclosure of which is incorporated herein by reference) and because intermediates I1, I2, and I4 are not observed in PAGE analysis of reactants and products (FIG. 5C). Using symmetry and DNA binding thermodynamics, it is possible to approximate two of the parameters: first, the spurious re-association rate of C and W is initiated by the same external 6 nt $\overline{5}$ domain as the correct association of C to substrate S, and consequently the rate constants should be similar. Thus, for the simulation it can be assumed that $k_3=k_1$. Second, the back-reaction of I3 and SB to re-form S and C is initiated by the same internal domain $\overline{5}$ (of length 4 nt) as the correct association of F to intermediate I3, so it can be approximated that $k_{-1}=k_2$.

Figure 7A:
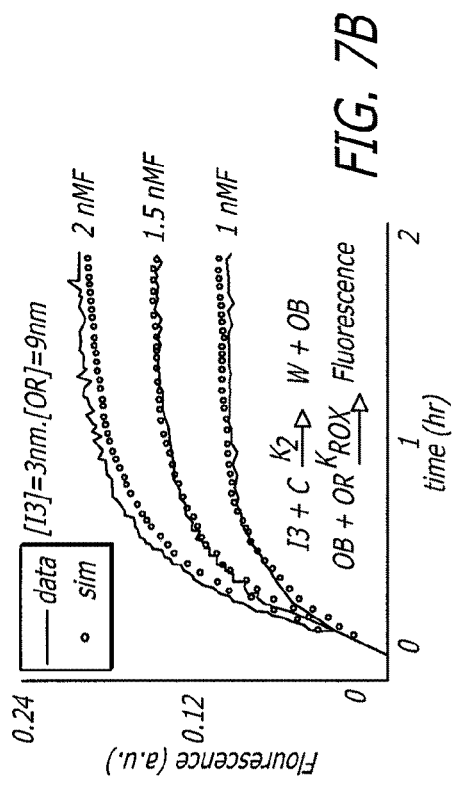
FIGS. 7a to 7d provide data from rate measurement experiments for the catalyst system of FIG. 5.
Figure 7B:
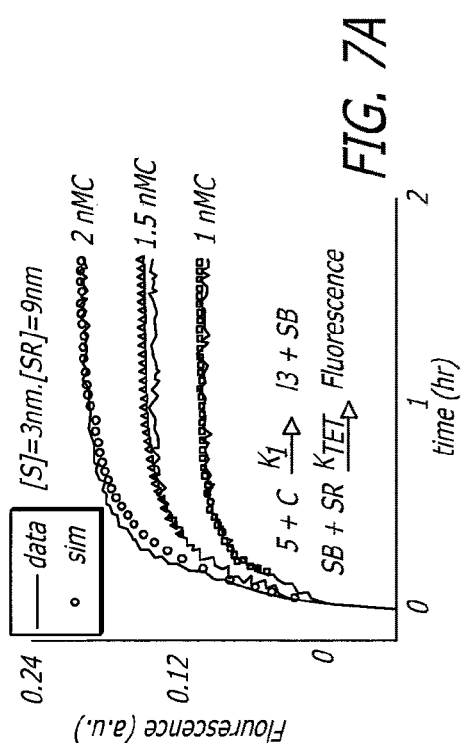
Figure 7C:
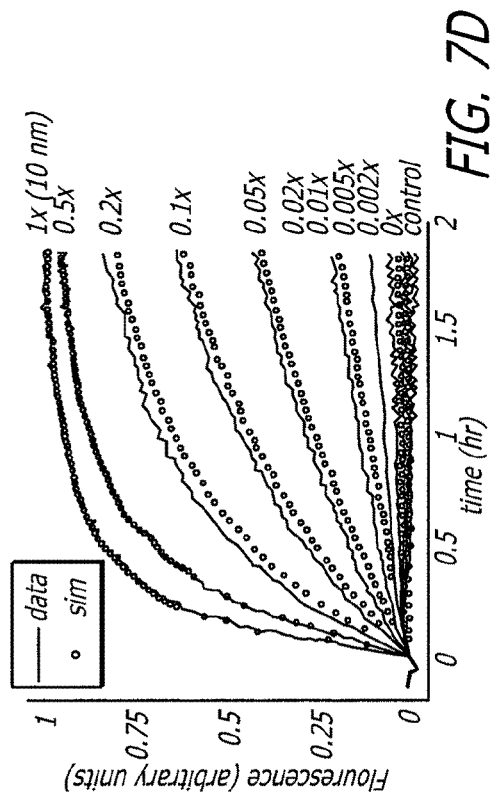
Figure 7D:
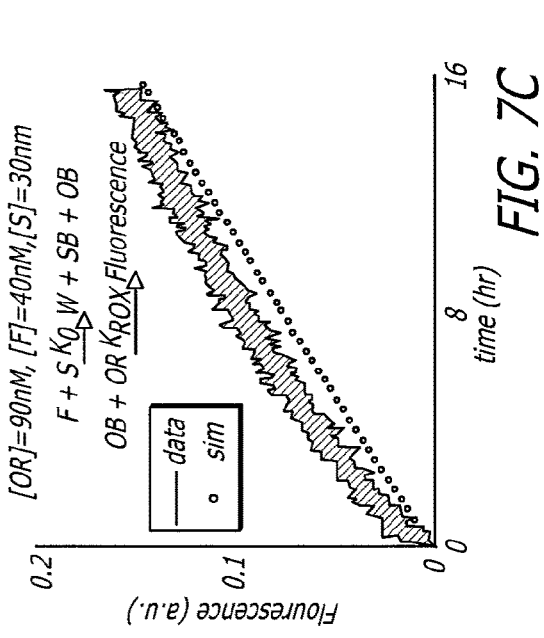

Using $k_{TET}$ and $k_{ROX}$ rate constants from the previous section, reaction rate constants $k_1$, $k_2$, and $k_0$ are directly measured to be $6.5 \cdot 10^5$, $4.2 \cdot 10^5$, and $2.3 \cdot 10^1\ M^{-1}s^{-1}$, respectively, as shown in FIGS. 7a to 7c. Specifically, FIG. 7a provides data on measurements of catalyst binding rate $k_1$. All traces contain 3 nM S initially, and different amounts of C were added at t≈0. Reporter SR was present at a 9 nM concentration. The dotted lines show simulation traces modeling reactions (1) and (4), assuming rate constant $k_1=6.5 \cdot 10^5\ M^{-1}s^{-1}$. FIG. 7b shows results from the measurement of fuel binding rate $k_2$. All traces contain 3 nM pre-prepared I3 initially, and different amounts of F were added at t≈0. Reporter OR was present at 9 nM concentration. The dotted lines show simulation traces modeling reactions (2) and (5), assuming rate constant $k_2=4.2 \cdot 10^5\ M^{-1}s^{-1}$. Finally, FIG. 7c provides a measurement of uncatalyzed reaction rate $k_0$, where [S]=30 nM, [F]=40 nM, no catalyst was present, and reporter OR was present at a 90 nM concentration. Again, dotted lines show simulation traces modeling reactions (2) and (3), assuming rate constant $k_0=2.3 \cdot 10^1\ M^{-1}s^{-1}$.

Note that for these experiments, the $k_{-1}$ rate of reverse reaction SB+I3 can effectively be ignored, because SB was consumed by reporter complex SR (simulations showed no visible difference when $k_{-1}$ was modeled). The last rate constant $k_3$ is difficult to measure because it is first-order, and the rate could not be slowed down to a time-scale where spectrofluorimeter readings would be meaningful. Thus, for the purposes of this analysis it was fitted using the results of the net kinetics of the catalytic system to be $4 \cdot 10^{-3}\ s^{-1}$. Using this analytic framework the time course of the catalyzed reaction over a wide range of catalyst concentrations is accurately reproduced by this reduced system of rate equations (FIG. 5e). According to this model, the addition of catalyst can accelerate the reaction by over four orders of magnitude ($k_2/k_0=1.8 \cdot 10^4$).

As shown in the reaction schematics provided in FIG. 5, in the net reaction each base pair that is broken is replaced by another of the same type, so the net free energy change from base-pairing interactions should be small. Instead, in this exemplary system the reaction is driven by the gain in configurational entropy corresponding to the liberation of OB and SB at the cost of localizing F. To confirm the dominance of this entropic driving force, F was truncated by removing up to 8 nt from its 5' end, making the products more and more thermodynamically disfavored.

To understand this result, consider the net reaction:

$$S+F \leftrightarrow OB+SB+W$$

The free energy change for this reaction, in dilute solutions, is given by:

$$\Delta G = \Delta G_{OB}° + \Delta G_{SB}° + \Delta G_W° - \Delta G_S° - \Delta G_F° + RT \ln Q^{def} = \Delta G_{net}° + RT \ln Q$$

where $Q=([OB]/c° \cdot [SB]/c° \cdot [W]/c°)/([S]/c° \cdot [F]/c°)$ is the reaction quotient relative to standard conditions and $\Delta G°_x$ is the standard free energy of species X at standard conditions, which here specify the TE buffer with 12.5 mM magnesium, 25° C., and $c°=1$ M.

The free energy change (the driving force for the reaction) decreases as concentrations change during the course of the reaction; once equilibrium is achieved, $Q=\exp\{-\Delta G°net/RT\}$ and $\Delta G=0$. If the standard free energy change $\Delta G°net \approx 0$, as would be expected for the reaction with the full-length fuel strand if the standard free energy is dominated by base pairing, then the driving force at any moment is just $RT \ln Q$. As a somewhat arbitrary reference point, the time at which half the substrate has been depleted can be considered. For the reaction in FIG. 8, this occurs when [S]=[F]=[SB]=[OB]=[W]=c=100 nM, $Q=10^{-7}$, and $RT \ln Q=RT \ln c=-9.6$ kcal/mol. For the reaction in FIG. 5e, c=5 nM and $RT \ln c=-11.4$ kcal/mol.

The free energy difference between the substrate S and the maximally truncated waste product W was approximated using the mFold server using DNA parameters for 25° C., with salt conditions being 10 mM Na+ and 12.5 mM Mg2+. Taking into consideration the 8 base pair stacks, external loops and dangles (due to the 1 domain in S, and the 3' overhang on the LB strand on the truncated waste product W), and an initiation entropy of 6.4 cal/mol/K per association, the predicted standard free energy change $\Delta G°_{net}$ for the (unfavorable) forward reaction is +11.7 kcal/mol.

Figure 8:
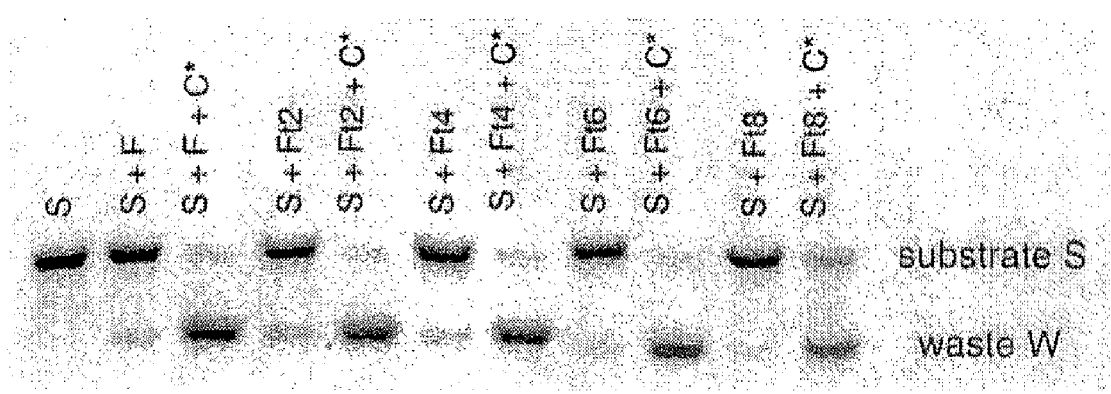
FIG. 8 provides a photographic plate of a gel measuring the entropic driving force of an exemplary catalyst system in accordance with the current invention.

According to these estimates, truncating the fuel strand F by 8 bases should disfavor the forward reaction enough that the equilibrium distribution possesses substrate S in excess of waste W. To verify the entropic driving force analysis was conducted by PAGE (12% native gel) of reactions with truncated fuel strands. In this experiment [S]=[F]=200 nM, [C]=20 nM, as denoted by the asterisk. All reactions were run at 25° C. for 3 hours. "Ft2" denotes that two bases were truncated from the 5' end of fuel strand F. However, the experiments described in FIG. 8 show waste in excess of substrate after 3 hours. This suggests that the estimate for $\Delta G°_{net}$ is too large; a value closer to +9 would be more compatible with the experiments. Nonetheless, as shown in FIG. 8, in all cases the waste product is favored at equilibrium.

Figure 9A:
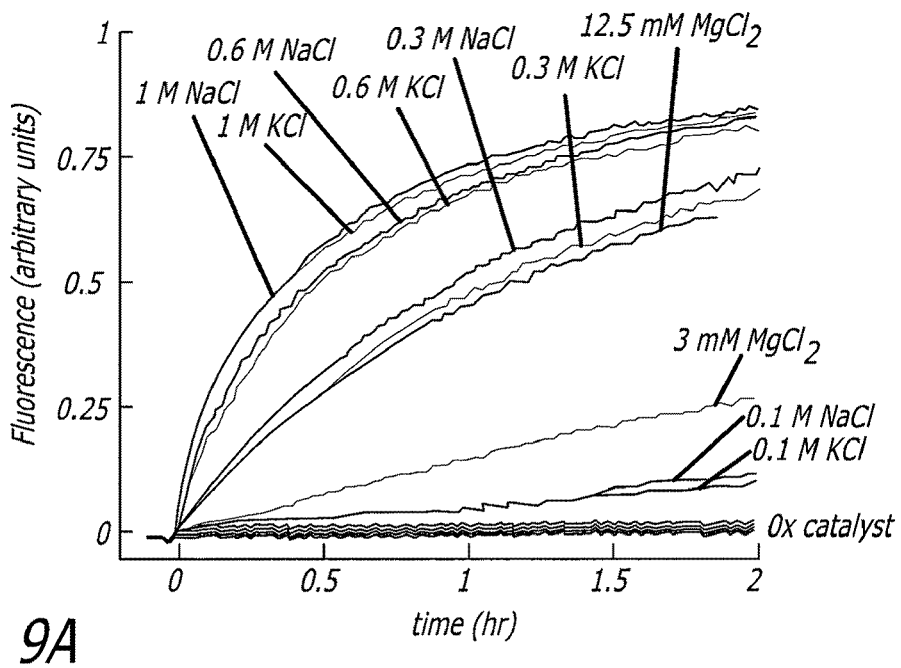
FIGS. 9a and 9b provide data from experiments on the robustness of the exemplary catalyst system of FIG. 5.

The thermodynamic driving force of the exemplary toehold catalyst, being dominated by center-of-mass configurational entropy of released molecules, is expected to be robust to environmental conditions such as temperature and salt concentrations that alter the strength of DNA hybridization. Specifically, salt conditions affect the free energy of hybridization (J. Santa Lucia, Proc Natl Acad Sci USA 95, 1460 (1998), the disclosure of which is incorporated herein by reference), but since there is no net gain or loss of base-pairs in a net reaction cycle, the equilibrium should not be significantly affected. The strength of the binding of the toehold domains still depend on the free energy of the base pairs formed, so salt concentration will affect the kinetics of the catalyzed pathway. However, the catalyst should qualitatively function across the range of salt concentrations, as long as the toehold domains still are able to co-localize the relevant strands. In FIG. 9*a*, it is demonstrated that catalytic function is preserved across a broad range of salt buffers, from 0.1 to 1 M concentrations. Specifically, the catalyst was tested here in TE supplemented with various different salt concentrations ([S]=10 nM and [F]=13 mM.) The flat traces at the bottom (controls run for every salt condition tested) show [C]=0, while all other traces have [C]=1 nM=0.1×. The reactions were run at 25° C. All traces shown were normalized to the same scaling factor. Although only salt concentration from 0.1 to 1 M, it should be understood that other tests have shown an even broader range of operation for the catalysts. For example, the catalyst system was tested in a Mg buffer down to 0.003 M, and theoretical analysis indicates that the catalyst should operate in a wide variety of salt concentration ranges, such as, for example, anything more than 0.1 M in a monovalent cation (sodium, potassium) or 0.001 M in a divalent cation (magnesium, manganese, nickel, zinc, etc) and up to a saturation level, such as 3 M.

Figure 9B:
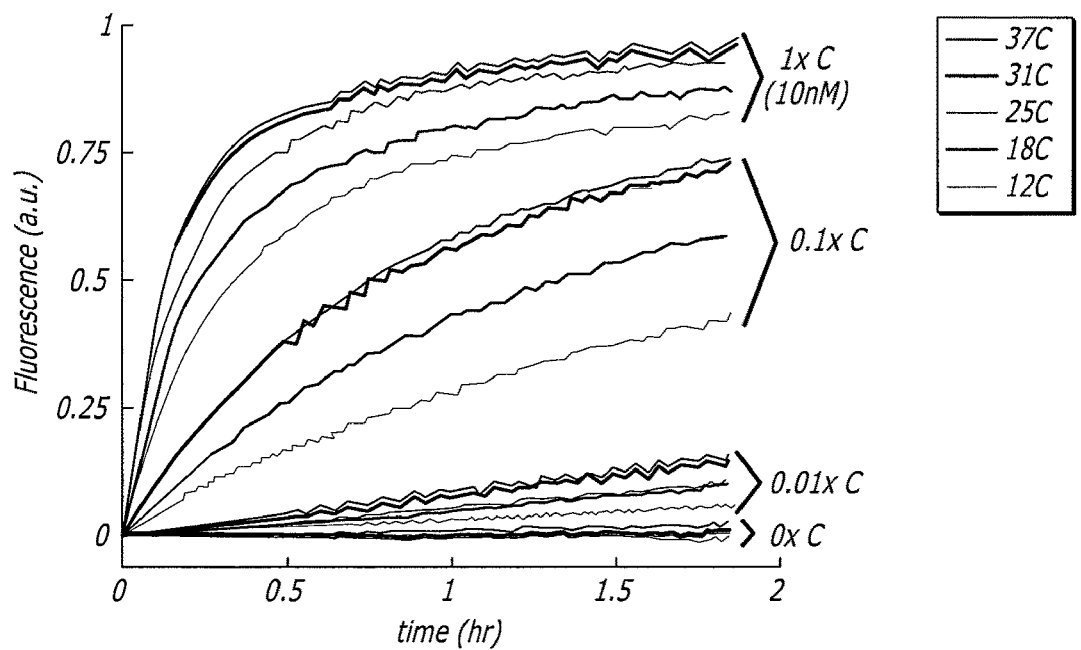

Meanwhile, temperature affects the equilibrium of a reaction only through the enthalpic change ($\Delta H°$). When the magnitude of the enthalpic change is small ($\Delta H° \approx 0$) as it is for the entropy-driven system, the effects of temperature have little effect on the reaction equilibrium although, again, they affect the kinetics of toehold-mediated processes. In FIG. 9*b*, the catalyst is shown to function across a 25 degree range of temperatures, from 12° C. to 37° C. In these tests the reactions were run in TE with 12.5 mM MgCl2. Note that the 18° C. and 25° C. traces show very similar kinetics for 0.1× C and 0.01× C, as do the 31° C. and 37° C. traces. To account for temperature-dependent fluorescence, traces were normalized individually with separate experiments (data not shown) that measured the fluorescence of the ROX fluorophore at different temperatures. Although only a temperature range of 12° C. to 37° C. was tested in the current example, other studies have shown activity of up to a temperature of 52° C., and analysis indicates that the catalytic system of the current system should theoretically operate in a temperature of from 0° C. to 65° C.

Finally, in addition to the relative insensitivity to the catalyst system of the current invention to environmental conditions such as salt concentration and temperature, it has also been demonstrated that the function of the DNA catalysts is relatively independent of substrate concentration. In exemplary studies the reaction was operational in substrate concentrations of from 1 nM to 100 nM, and theoretical analysis indicates that such reactions should operate in substrate concentrations of from about 1 pM and 10 µM.

Example 2

Cascaded Networks

In order for an engineered catalyst system to be integrated into large circuits for complex dynamic behavior, it is essential that several instances of the catalyst system can be cascaded. As a first proof-of-principle example, two two-layer feed-forward circuits are constructed by designing second catalyst systems with outputs containing a subsequence that acts as the catalyst for the original systems described in Examples 1a and 1b above. Specifically, FIG. 10 provides a cascaded network based on the catalyst system of Example 1, the schematic of which is provided in FIG. 5*a*.

As shown in FIG. 10, in one exemplary embodiment of a cascade network based on the catalyst system of FIG. 5, catalyst C0 catalyzes the production of OB0 (which contains a subsequence identical to C from FIG. 5), which in turn catalyzes the production of OB1. For clarity, F, OB, and the other reactants and products from FIG. 5 are relabeled F1, OB1, and so forth. See Table 2, below, for sequences of new domains.

TABLE 2

Domain Sequences

| Domain | Sequence | Length |
|---|---|---|
| 1 | 5'-CTTTCCTACA-3'<br>(SEQ ID 1) | 10 |
| 2a (=x) | 5'-CCTACG-3' | 6 |
| 2b (=y) | 5'-TCTCCA-3' | 6 |
| 2c | 5'-ACTAACTTACGG-3'<br>(SEQ ID 2) | 12 |
| 3 | 5'-CCCT-3' | 4 |
| 4a | 5'-CATTCAATAC-3'<br>(SEQ ID 5) | 10 |
| 4b (=x) | 5'-CCTACG-3' | 6 |
| 5 (=y) | 5'-TCTCCA-3' | 6 |
| 6 | 5'-CCACATACATCATATT-3'<br>(SEQ ID 4) | 16 |
| 7 | 5'-TACTTATTAGCC-3'<br>(SEQ ID 6) | 12 |
| 8 | 5'-GACA-3' | 4 |
| 9a | 5'-CTACTTTCAC-3'<br>(SEQ ID 7) | 10 |

TABLE 2-continued

Domain Sequences

| Domain | Sequence | Length |
|---|---|---|
| 9b (=x) | 5'-CCTACG-3' | 6 |
| 10 (=y) | 5'-TCTCCA-3' | 6 |

The concentration of upstream catalyst C0 is constant, so initially [OB0] increases linearly with time, which causes [OB1] to increase quadratically with time (FIG. 10b). Eventually, the substrates and fuels are depleted, and the reaction halts, giving rise to an overall sigmoidal shape to the fluorescence traces (FIG. 10b). With regards to the fluorescence results, the indicated amounts of initial catalyst C0 were added at t≈0. Fluorescence derives from reporter complex OR (FIG. 5d) at 30 nM. Dotted lines show simulated traces and "a.u." stands for arbitrary units. The inset of the figures shows a response to 0.0010×, 0.0003×, and 0.0001× catalyst. The asterisk indicates that three independent reaction traces are shown. In the figure, 1.0 fluorescence units correspond to ≈10 nM of triggered reporter.

Figure 11:
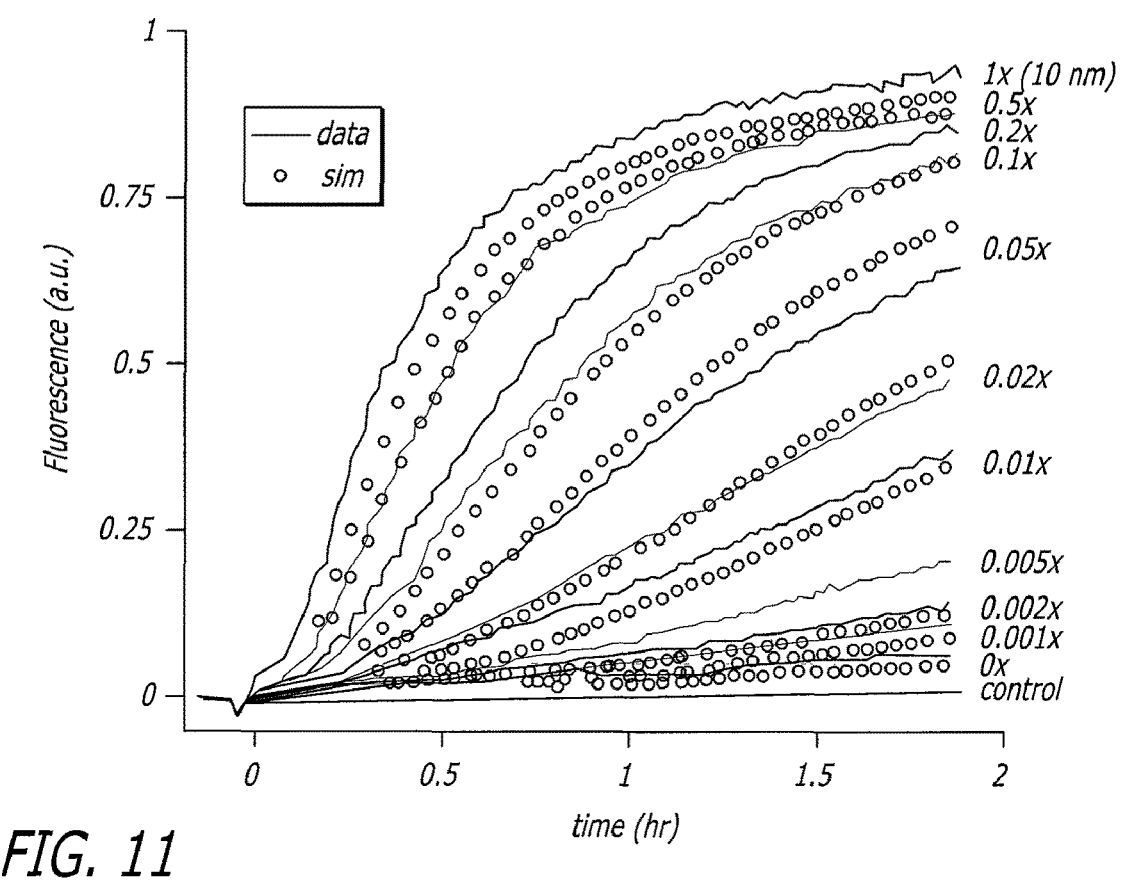
FIG. 11 shows data from rate studies conducted on the network in FIG. 10.

As mentioned, the downstream layer catalyst system of FIG. 10 is identical to that presented in FIG. 5c, and thus the same rate parameters can be used for it as were used in FIG. 5e. The remaining parameters for the upstream catalyst system are fitted to the quadratic series data, with the same constraints k10=k−30 and k−10=k20. From rate studies conducted on the network, and shown in FIG. 11, it can be seen that the rates were quantitatively similar (though somewhat slower) to the rates of the analogous reactions in the upstream system, which supports the previous explanation of the behavior of the circuit. Specifically, as seen in the gel in FIG. 5c, some impurity fraction of the substrate S reacts very quickly to fuel F. Evidence for this is also seen in FIG. 5e, where the fluorescence value of the "0×" trace is slightly higher after the addition of fuel F at t≈0. For the quadratic feed-forward circuit, a small constant amount of OB0 released from the upstream system would be converted into a small constant production rate of OB1. This initial concentration [OB0] was fitted to be 45 pM, for a total of 4 additional fitted parameters.

This cascaded system can also be used as an amplifier to detect small quantities of C0. Repeated fluorescence experiments show that it is possible to distinguish reliably between 1 pM (0.0001×) catalyst C0 and 0× catalyst within 12 hours (FIG. 10b, inset). This corresponds to a roughly 900-fold amplification of the input signal. (1 pM of catalyst triggered≈900 pM of reporter above the baseline set by the 0× reaction.) For comparison, 1 pM corresponds to about one molecule per eukaryotic cell volume. Repeated measurements of independent samples show less than 3% variability across all timepoints, which as discussed below can be the result of normal fluorescence variability.

Several factors can reduce the repeatability of fluorescence experiments: First, the spectrofluorimeter luminosity output differs from lamp bulb to lamp bulb and luminosity tends to decrease as any particular lamp bulb ages. Second, different preparations of purified substrate complexes S, though nominally calibrated to the same concentration, in practice differed in purity. Third, fluorophores tend to bleach, and thus older stocks tend to give lower fluorescence readings for the same concentration. Finally, the Eppendorf pipettors used in these studies are high precision but low accuracy; thus using two different pipettors to measure the same volume would often yield different pipetted quantities.

To minimize these effects the following steps were taken for all fluorescence experiments displayed:
- All traces within a figure were performed in a single sitting;
- All traces within a figure used the same stocks of all purified samples, including reporter complexes and substrate complexes; and
- All traces within a figure used the exact same pipettor for each quantity measured (i.e., dedicated pipettor for 6 µl, another dedicated pipettor for 15 µl, etc).

The domains involved in the quadratic feed-forward circuit shown in FIG. 10a and the autocatalytic reaction to be discussed later are shown in Table 2. As mentioned above, there is a significant amount of domain redundancy, because the initial catalyst, quadratic circuit, and autocatalyst circuit were designed simultaneously with the goal of minimizing the number of changes between designs. Again, it should be understood that in designing a catalytic reaction system in isolation, the domains can be completely independent. Specifically, a design in which OB and C possess independent sequences is shown in FIG. 12. The sequences of the system of FIG. 12 are shown in Table 3, below.

TABLE 3

Independent Input/Output Catalyst System Sequences

| Strand | Length | Domain Abstraction | Sequence |
|---|---|---|---|
| IndCat-F | 44 | 12 13 14 15 | 5'-ACCACATCAATCTCGATCCA GTACACCTCTTCACGAACATTTC A-3' (SEQ ID 8) |
| IndCat-LB | 50 | 16 15 14 13 12 | 5'-TGGCTATGAAATGTTCGTG AAGAGGTGTACTGGATCGAGAT TGATGTGGT-3' (SEQ ID 9) |
| IndCat-SB | 20 | 14 15 | 5'-ACCTCTTCACGAACATTTC A-3' (SEQ ID 10) |
| IndCat-OB | 34 | 11 12 13 | 5'-ACCTAATAGCACCACATCA ATCTCGATCCAGTAC-3' (SEQ ID 11) |
| IndCat-C | 22 | 15 16 | 5'-CTTCACGAACATTTCATAG CCA-3' (SEQ ID 12) |
| IndCat-OF2 | 20 | F 11 12 | 5'-/TAMRA/ACCTAATAGCAC CACATCAA-3' (SEQ ID 13) |
| IndCat-OQ2 | 27 | 13t 12 11 Q | 5'-ATCGAGATTGATGTGGTGC TATTAGGT/IAbRQ/-3' (SEQ ID 14) |

This catalyst system functions almost identically to the one presented in FIG. 5A. Modularity is facilitated by sequence independence of the input (catalyst) and output (product); it is for this reason that strand SB is not also labeled as an output, even though it is also catalytically released by C. The design of the catalysis reaction enforces some degree of sequence similarity between strands SB and C, and this limits its usefulness in the construction of larger-scale circuits.

Figure 13A:
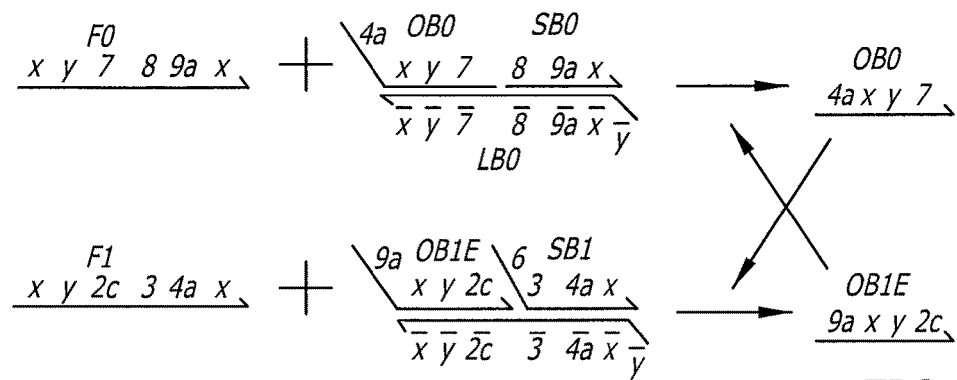
FIGS. 13a and 13b show schematics of the mechanism and test results for an exemplary cross-catalyst circuit formed using the toehold DNA catalyst in FIG. 5.

Finally, feedback in this two-layer circuit can be achieved by redesigning OB1 so that it can, in turn, catalyze the F0+S0 reaction. A schematic of such a circuit is shown in FIG. 13a. Recall that domains 2a, 4b, and 9b are identical to each other, and renamed x here. Domains 2b, 5, and 10 are identical to each other, and renamed y here. Thus, the design is actually very similar to that of the feed forward quadratic circuit, the only difference being that the OB1 output strand has been replaced by OB1E, possessing the 9a domain at its 5'-most end, rather than the 1 domain.

Figure 13B:
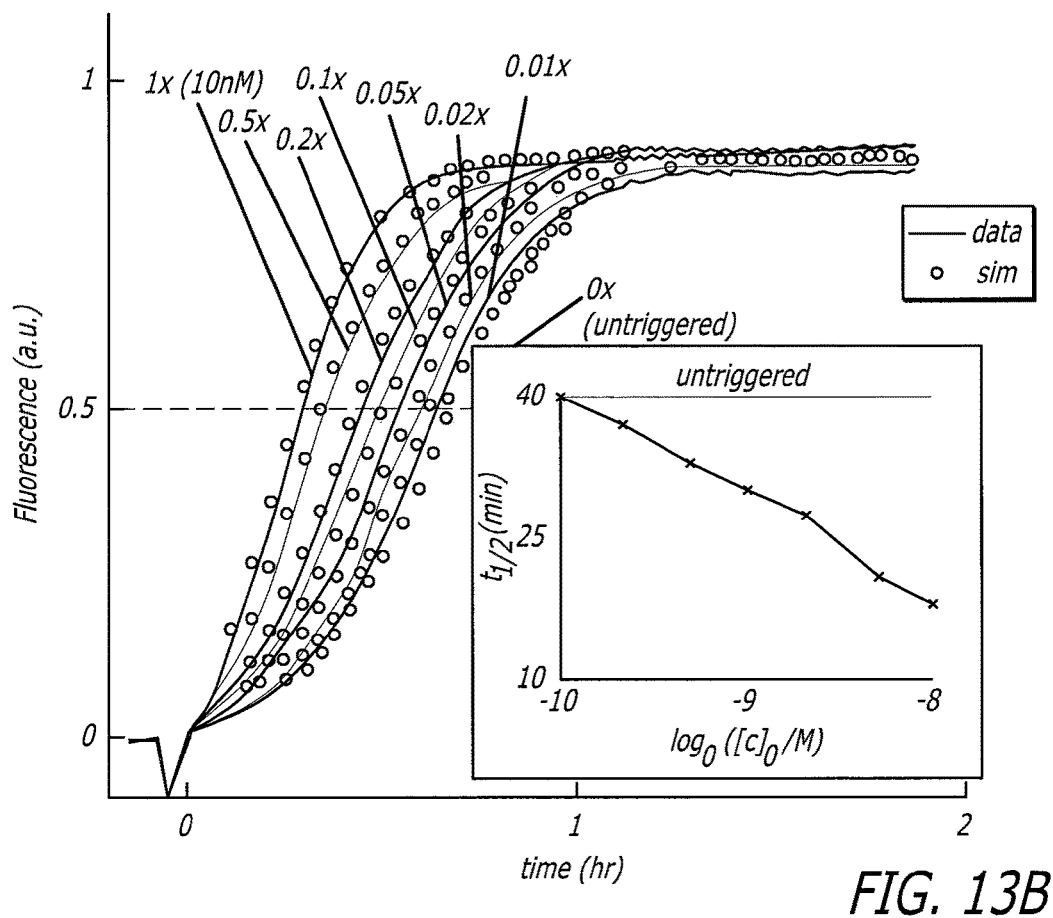

Feedback in this cross-catalytic system causes the concentrations of both OB0 and OB1 to grow exponentially at early times, as is shown in kinetic data from fluorescence studies provided in FIG. 13b. As will be discussed in greater detail below the cross-catalyst system is more leaky than the auto-catalyst system, and 1% trigger is indistinguishable from the untriggered reaction. The reactions used in the modeling of the cross-catalyst system are shown below:

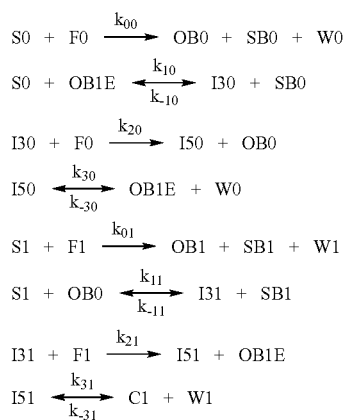

As illustrated above, the only difference between the cross-catalytic circuit and the feed-forward circuit is the identity of the 5' domain of the OB1 strand; this difference should not affect any rate constants, so the rate constants used in simulations are exactly the same as those used for the quadratic feed-forward circuit. The only additional parameter that needs to be fit is the effective initial concentrations of OB0 and OB1E. FIG. 13b shows the fits with initial concentrations [OB0]=[OB1E]=280 pM.

Example 3

Autocatalyst

Although embodiments of "feedback" networks capable of producing exponential kinetics are provided above, such kinetics can also be achieved with a much smaller autocatalytic system by modifying the substrates S of the catalyst systems presented in FIG. 5 such that the output molecule domain contains a catalyst strand as a subsequence. Because the production rate of such systems would be proportional to its own concentration, the system would inherently exhibit exponential growth. Feedback is an important feature of both biological regulatory networks and artificial control circuits because of the desirability of obtaining exponential growth kinetics.

Figure 14A:
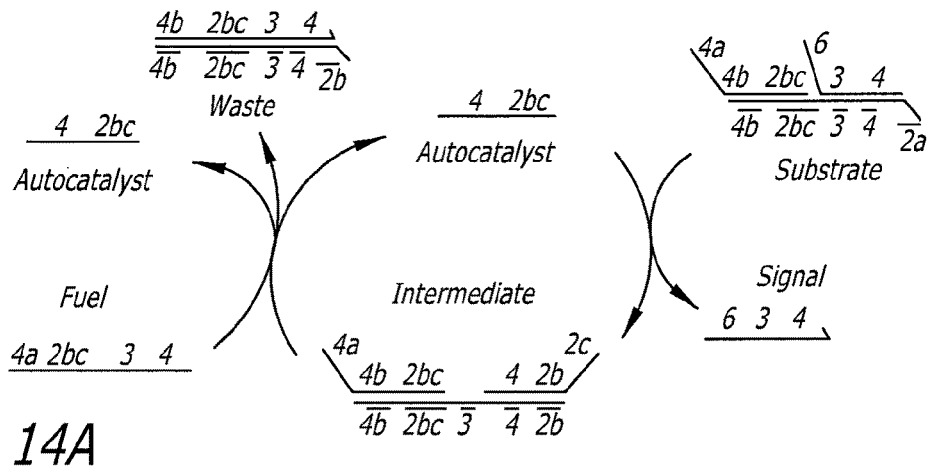
FIGS. 14a to 14e show schematics of the mechanism and test results for an exemplary autocatalyst formed using the toehold DNA catalyst in FIG. 5.
Figure 14B:
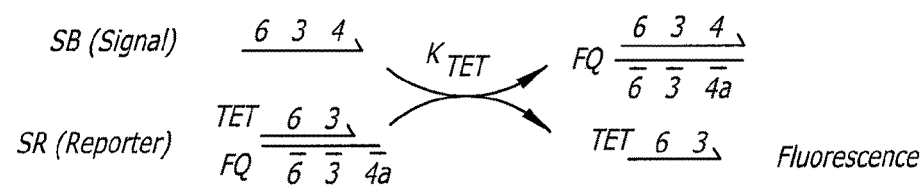
Figure 14C:
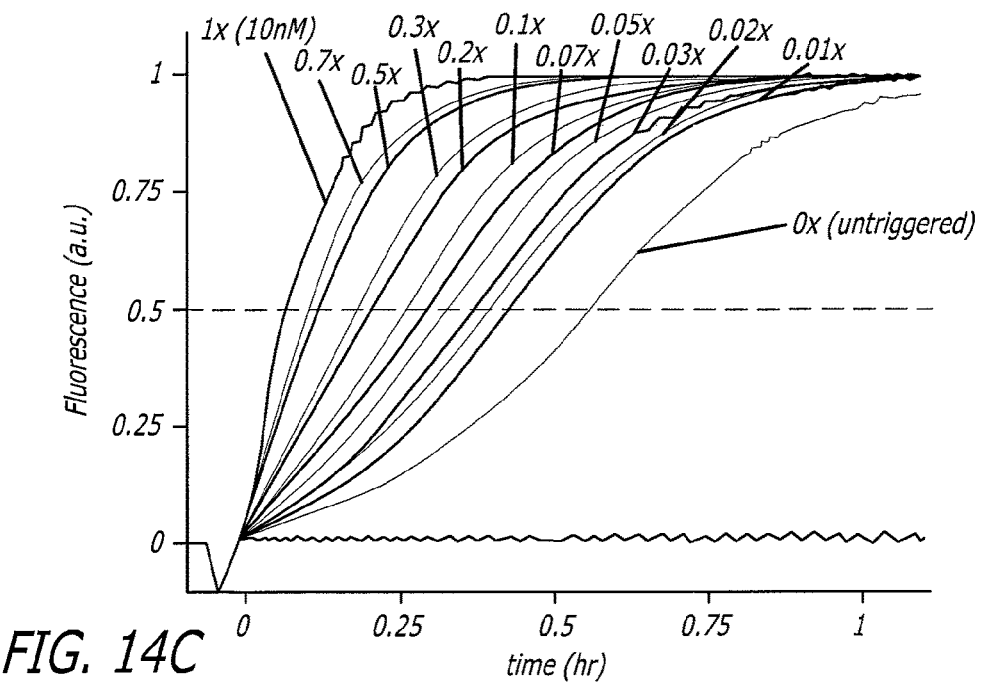

In one exemplary embodiment, exponential growth kinetics are achieved by redesigning the reaction presented in FIG. 5 such that output OB contains catalyst C as a subsequence, as shown in FIG. 14a). The reaction is then autocatalytic. FIG. 14c shows the time course of this reaction for a wide range of catalyst concentrations. In a process dominated by initial exponential growth ($c \approx c_0 e^{\lambda \tau}$), the time to reach a threshold degree of completion depends logarithmically on the initial concentration $c_0$ (where c is the concentration of the exponentially growing species, $\lambda$ is the characteristic time constant, and t is time). Thus, a linear trend in a log-linear plot of initial concentration to time to half completion (t$\lambda$/2) is indicative of exponential growth. [Such plots are used as calibration standards for quantitative methods such as real-time polymerase chain reaction (PCR). (See, R. Higuchi, C. Fockler, G. Dollinger, R. Watson, Nat. Biotechnol. 11, 1026 (1993), the disclosure of which is incorporated herein by reference.)]

Figure 14D:
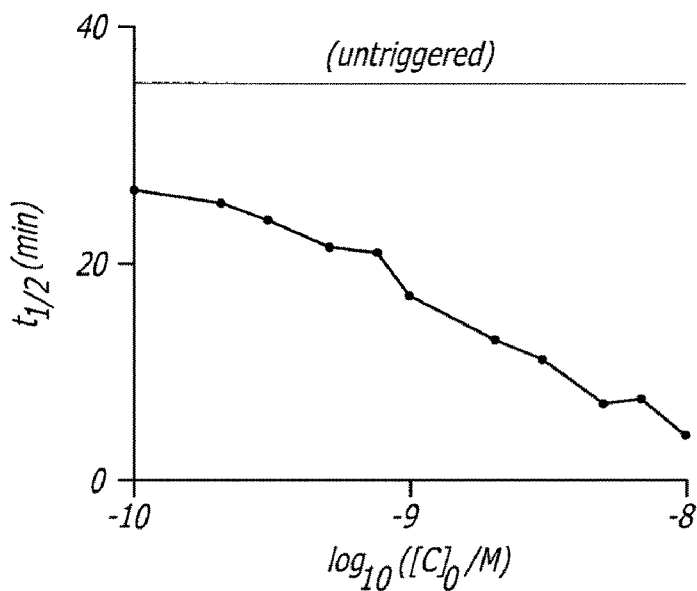

FIG. 14d shows that the exemplary autocatalytic system has this characteristic behavior, implying that exponential growth kinetics have indeed been achieved and that the reaction is not substantially affected by product inhibition. Further confirmation comes from the quality of fit to the data of a model based on rate constants derived for the catalyst system of FIG. 5. It should be noted that for the autocatalytic system, reporter complex SR is used to measure the progress of the reaction, because reacting OB with OR might damp the exponential reaction. The reactions used to model the behavior of the autocatalyst are shown below:

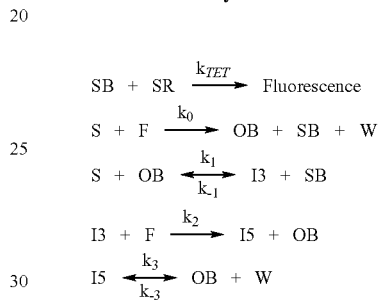

Parameters $k_{TET}$, $k_0$, $k_1$, $k_{-1}$, $k_2$, and $k_{-3}$ again are the same as measured previously. Parameter $k_3 = 4 \cdot 10^{-3}$ s$^{-1}$ is the same as fitted to the catalyst data in FIG. 5e. The only new parameter fitted is the impurity concentration, the initial concentration of [OB]=460 pM. Purification of the autocatalyst substrate was significantly more difficult technically than that of the catalyst substrate, as evidenced by different inferred initial [OB] for different purified samples. With reference to the current embodiment, reporter complex SR, was used for monitoring autocatalytic and cross-catalytic reaction networks, TET denotes the tetrachlorofluorescein fluorophore, and FQ denotes the Iowa Black Fluorescent Quencher. In FIG. 14c, indicated amounts of autocatalyst were added at t≈0. At 30 min, 1% (100 pM) was amplified 25-fold over the untriggered reaction. Reporter SR was present at 20 nM=2×. Control sample contained no fuel F. FIG. 14d shows a semi-log plot of t1/2 (in minutes) as a function of logarithm of molar trigger concentration. The line labeled "untriggered" shows t1/2 of the untriggered reaction.

Largely because of their relevance to the origin of life and to the RNA world, autocatalytic and cross-catalytic self-replication reactions have been proposed and demonstrated previously. (See, e.g., R. F. Gesteland, T. R. Cech, J. F. Atkins, Eds. The RNA World: The Nature of Modern RNA Suggests a Prebiotic RNA World (Cold Spring Harbor Laboratory Press, Cold Spring Harbor, N.Y., ed. 3, 2006); and N. Paul, G. F. Joyce, Curr. Opin. Chem. Biol. 8, 634 (2004), the disclosures of which are incorporated herein by reference.) However, such systems typically suffer from product inhibition and thus exhibit parabolic, rather than exponential, growth kinetics. Recent exceptions include cross-catalytic deoxyribozymogens (M. Levy, A. D. Ellington, Proc. Natl. Acad. Sci. U.S.A. 100, 6416 (2003), the disclosure of which is incorporated herein by reference) and catalyzed self-assembly (P. Yin, H. M. T. Choi, C. R. Calvert, N. Pierce, Nature, in press, the disclosure of which is incorporated herein by reference) based on the hybridization chain reaction (R. M. Dirks, N. A. Pierce, Proc. Natl. Acad. Sci. U.S.A. 101, 15275 (2004), the disclosure of which is incorporated herein by reference); as described herein the current autocatalyst system is substantially faster than these prior art systems. This increase speed is the result of the reduced spontaneous activity of the circuit (for example, by improved purification of the substrate complex), and is important to ensure that the system can be used as an enzyme-free constant-temperature alternative to PCR for detecting known sequences.

Figure 14E:
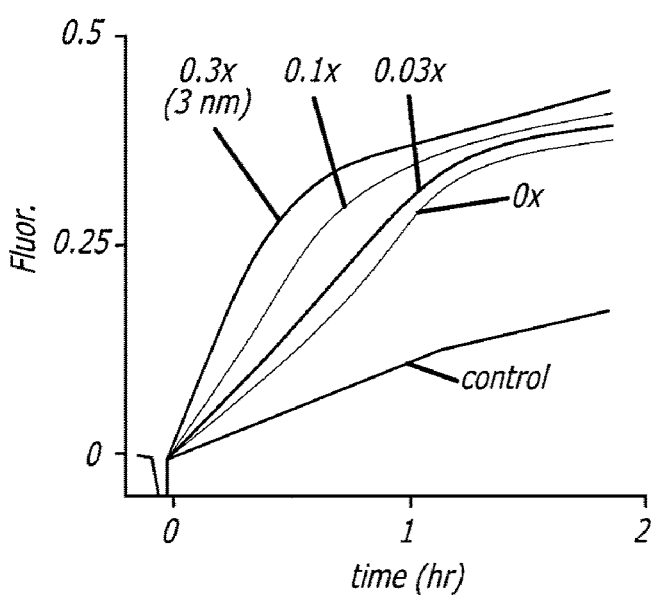

For many applications in biotechnology, nucleic acid devices must remain functional in the presence of naturally occurring macromolecules. The autocatalyst system of the current invention was therefore tested in the presence of an excess of mouse liver total RNA with rabbit reticulocyte lysate (FIG. 14e). As shown, reactions proceeded to apparent completion with no more than a twofold slowdown, and the presence of a 3% trigger can still be detected. The total RNA present in solution was 10× (by mass) that of the sum of all relevant catalyst DNA. Active cell lysate, as would be used in an in vitro translation system, was added to be 1.1% by volume of total reaction (17 mL in 1500 mL). The control reaction did not contain any substrate S. Experiments involving total RNA but not cell lysates did not show the observed drift.

Example 4

Allosteric Catalyst

To establish greater control over kinetics of catalysis, it is possible to model the action of DNA nanomotors. In those constructions, a DNA molecule is able to switch between several different states upon the exogeneous addition of actuator strands. This idea can be incorporated into the catalyst system of the current invention in the form of an allosteric catalyst that adopts one of two hairpin configurations (see FIG. 15a). As shown in FIG. 15a, one of the two hairpin configurations (the active state) is energetically favored normally, but the allosteric catalyst can be driven to the other hairpin state with addition of the inhibitor strand aCi. The inactive allosteric catalyst will spontaneously rearrange into its active state when the inhibitor strand is displaced by the activator strand. The allosteric catalyst is the first demonstration of integrating a DNA nanomotor with a DNA catalyst. Furthermore, since the allosteric catalyst is a single strand of DNA, this construction is also a hallmark in that it is a minimal DNA-based nanomotor. FIG. 15b provides evidence that the allosteric catalyst dynamically switches between the active and inactive states as shown by the change in the rate of the catalyzed reaction. The data in FIG. 15b has been smoothed in this subfigure with a radius of 40 points. FIG. 15b, inset 2, shows a plot of the sigmoidal activation function, given constant inhibitor, where [aC]=1 nM=0.1×, [aCi]=10 nM=1×. (c).

Figure 15C:
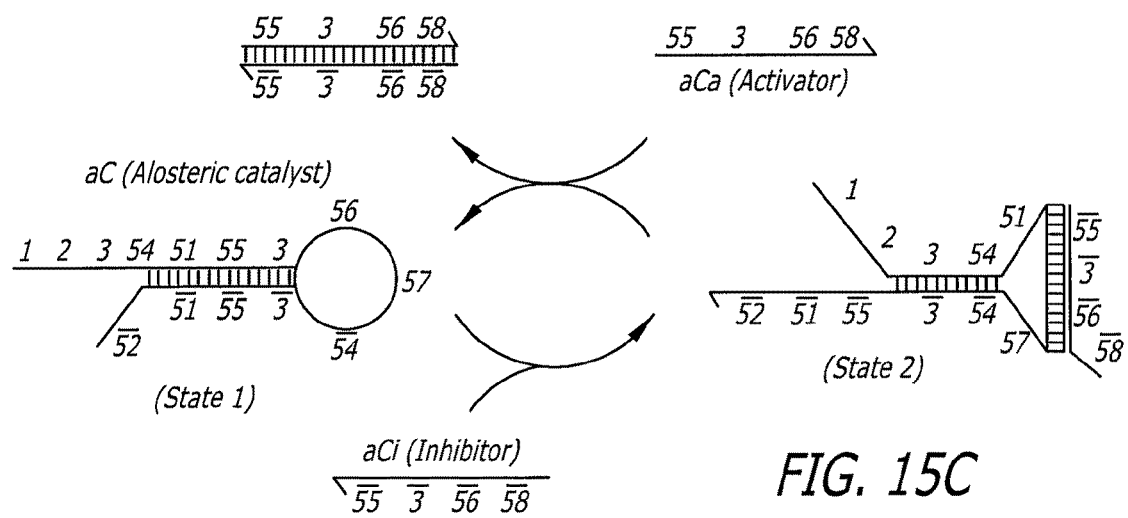

Building upon the work of the allosteric catalyst presented in FIG. 15a, another version of the allosteric catalyst was then constructed that functions to catalyze a different reaction in each state (see FIG. 15c). While many previous DNA nanomotors constructions exist, they all switch between one active and one inactive state. Here a variant on the allosteric catalyst is shown that can serve useful function in both states (catalyzing a different reaction in each state).

Example 5

Catalytic Logic Systems

In previous work in vitro logic gates have been constructed from DNA complexes based on hybridization kinetics. These gates, however, are stochiometrically consumptive, and are difficult to integrate into complex networks without robust signal restoration. In the current example designs are presented for catalytic logic gates using the entropy drive DNA catalyst system, such that the inputs act as catalysts and are not consumed.

Figure 16A:
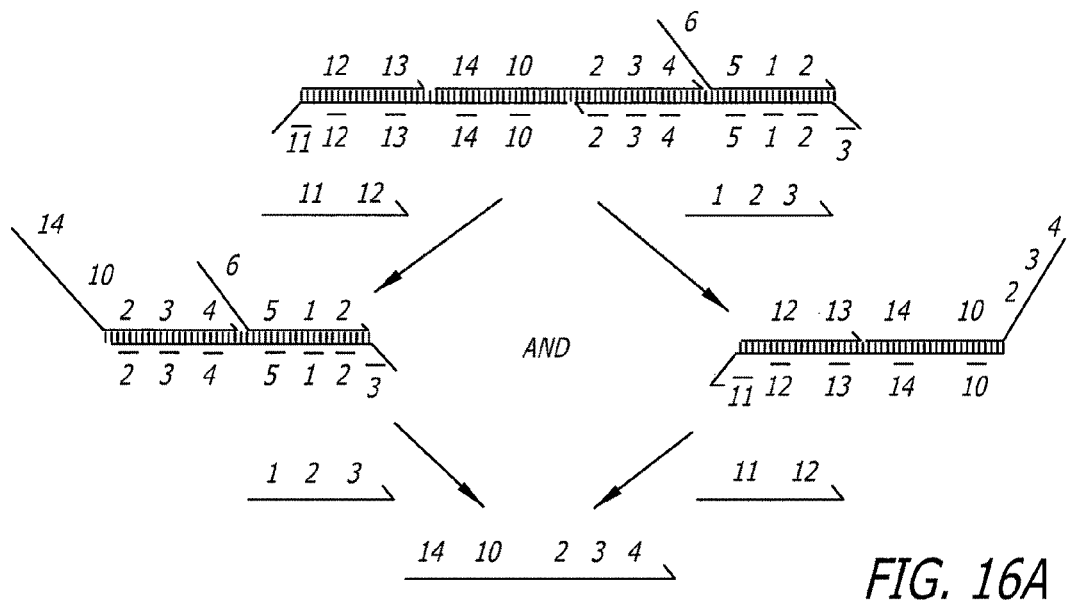
FIGS. 16a and 16b show schematics of the mechanism for exemplary catalytic logic gates formed using the toehold DNA catalyst in accordance with one embodiment of the current invention.
Figure 16B:
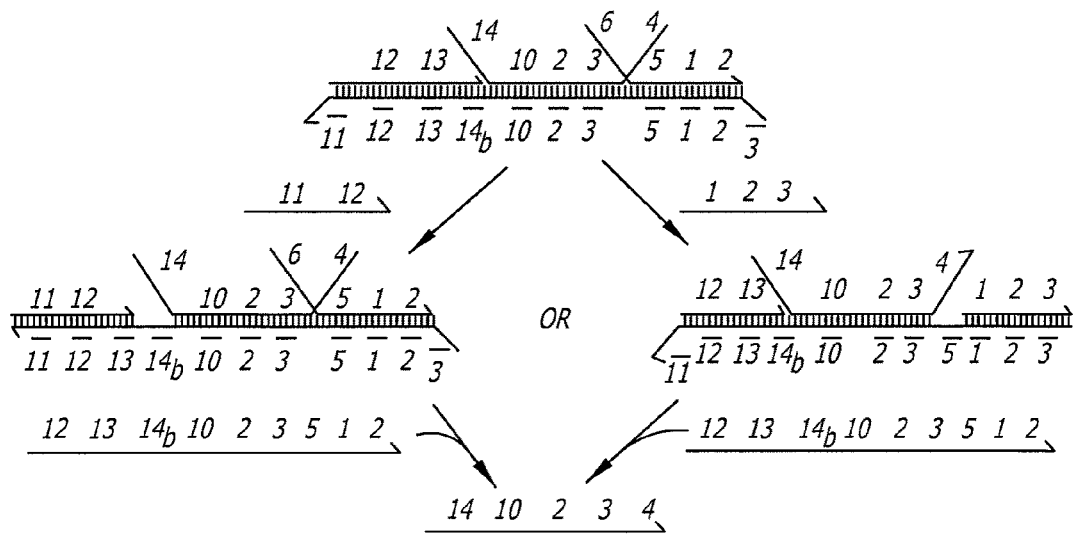

The ability to construct larger circuits will enable the wide range of chemical circuit functions needed for sophisticated applications. The current toehold exchange catalytic reaction networks are suited for scaling up to larger circuits. The modular molecular design makes synthesis of more complex components and networks with arbitrary topology straightforward. To demonstrate this, schematics for logical AND and OR gates are presented in FIG. 16. In an entropy-driven catalytic analog AND gate both of two catalysts are required to release output, in an OR gate only one must release an output.

Figure 17A:
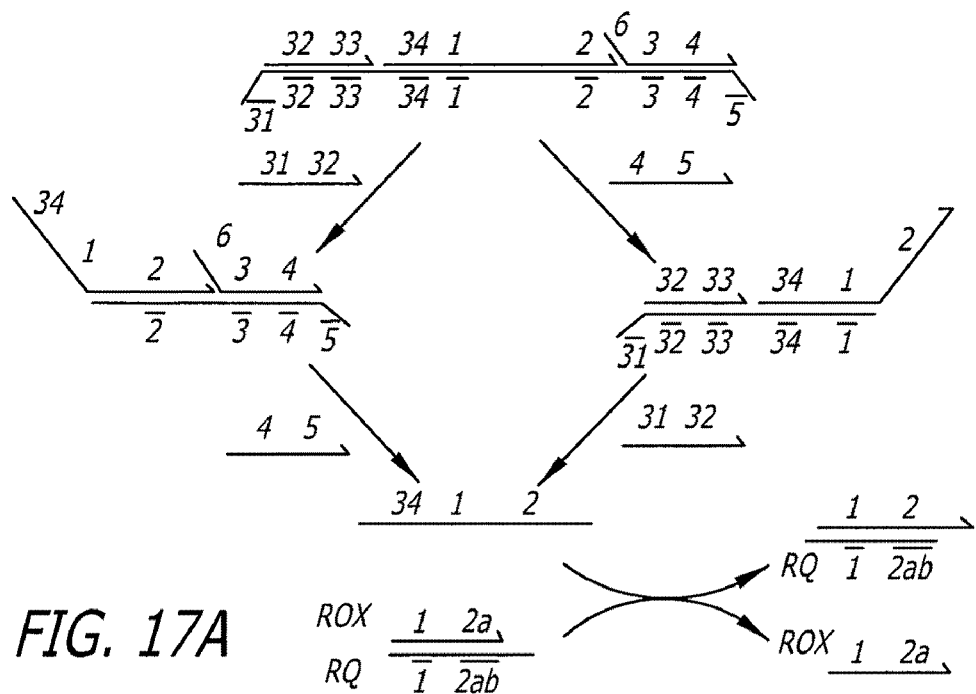
FIGS. 17a and 17b show schematics of the mechanism and test results for an exemplary AND gate formed using the toehold DNA catalyst of the current invention.
Figure 17B:
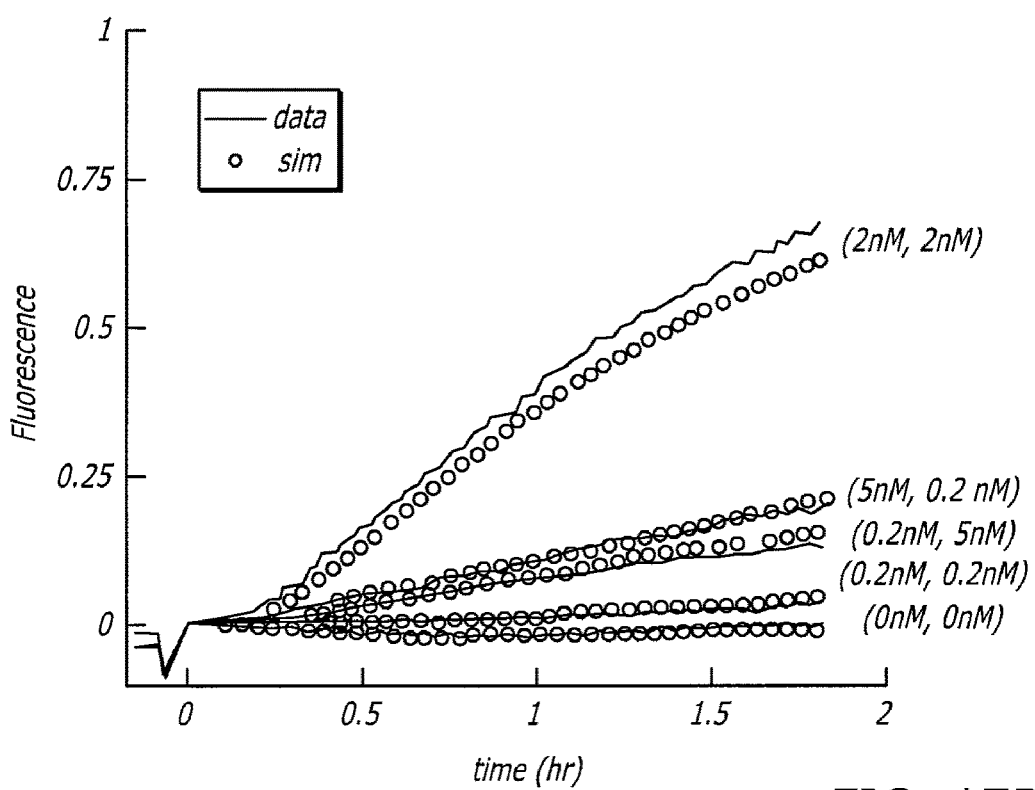

A functional embodiment of an AND gate and experimental results for the logical AND gate function are shown in FIGS. 17a and 17b. FIG. 17a shows a reduced schematic of the function of the AND gate, where fuel strands $\bar{3}$ $\bar{2}$-$\bar{3}$ $\bar{3}$-$\bar{3}$ $\bar{4}$-$\bar{1}$ and 2-3-4 (not shown) displace the 5' and 3' regions of the output strand 34-1-2 from the respective linking strands, and these reactions are catalyzed by strands 31-32 and 4-5. When both the 5' and 3' ends of the output strand are released, it reacts with the reporter complex (same as in FIG. 5D) and fluorescence increases. More specifically, in the example shown in FIG. 17a, the output strand (34-1-2) is sequestered on both the 5' and 3' ends in the substrate. The catalysts 31-32 and 4-5 function independently to release the 5' and 3' ends, respectively, of the output. This action requires fuel strands $\bar{3}$ $\bar{2}$-$\bar{3}$ $\bar{3}$-$\bar{3}$ $\bar{4}$-$\bar{1}$ and 2-3-4 (not pictured). Only when both ends are released is the output strand able to react with the reporter complex. (In the right-hand pathway, single-stranded domain 2 can interact with the reporter complex, but initiation of four-way branch migration through helical domains 1, which could in principle complete triggering of the reporter, is sufficiently slow as to be negligible in practice.) The design is symmetric, despite appearances; domains 34 and 1 always appear together, and their lengths sum to the same as that of domain 2 (24 nt). (The domains are labeled separately only for historical reasons to clarify interactions with the complex.)

The multiplicative (AND-like) behavior can be understood quantitatively as follows: the left (5') and right (3') catalytic ends operate independently and follow approximately the same kinetics as the catalyst system of FIG. 5. Let $f_L(t)$ be the fraction of left ends that have reacted with the fuel strand $\bar{3}$ $\bar{2}$-$\bar{3}$ $\bar{3}$-$\bar{3}$ $\bar{4}$-$\bar{1}$, and let $f_R(t)$ be the fraction of right ends that have reacted with the fuel strand 2-3-4. Then the fraction of output strand that has been released on both ends, and thus made active, is $f_{out}(t) = f_L(t) \cdot f_R(t)$. At initial times, when catalytic activity is linear in catalyst strand concentrations x and y, we thus have $f_{out}(t) \approx M\,xyt^2$ for some constant M. Consequently, at a fixed time (prior to saturation), the output concentration is proportional to the product of the input concentrations. In the fluorescence verification data [S]=10 nM, [F1]=[F2]=13 nM. As shown ([C1], [C2])=(2 nM, 2 nM) is more effective at releasing output than (5 nM, 0.2 nM) and (0.2 nM, 5 nM) even though the latter combinations possess higher total catalyst concentration.

As the 3' region of the output and the substrate are very similar to the system given in FIG. 5, the same reaction rates were used here for simulation. For the reaction rates relevant to the 5' catalytic component, the same rate constants were used as for the quadratic feed-forward circuit, taken as "typical" values. That is, the reactions rates were not fitted to the data given here, even though the reaction rates most likely differ, since the sequences for the left end of the AND gate are quite different from those of the upstream catalyst of the quadratic circuit. New domain sequences are given in Table 4, below.

TABLE 4

Domain Sequences for the Catalytic AND Gate

| Domain | Sequence | Length |
|---|---|---|
| 31 | 5'-CACACA-3' | 6 |
| 32 | 5'-ACTTCAGTCATTAAGC-3' (SEQ ID 15) | 16 |
| 33 | 5'-AGAC-3' | 4 |
| 34 | 5'-CCATACAAGTATCA-3' (SEQ ID 16) | 14 |

Example 6

Superexponential Circuits

Figure 18:
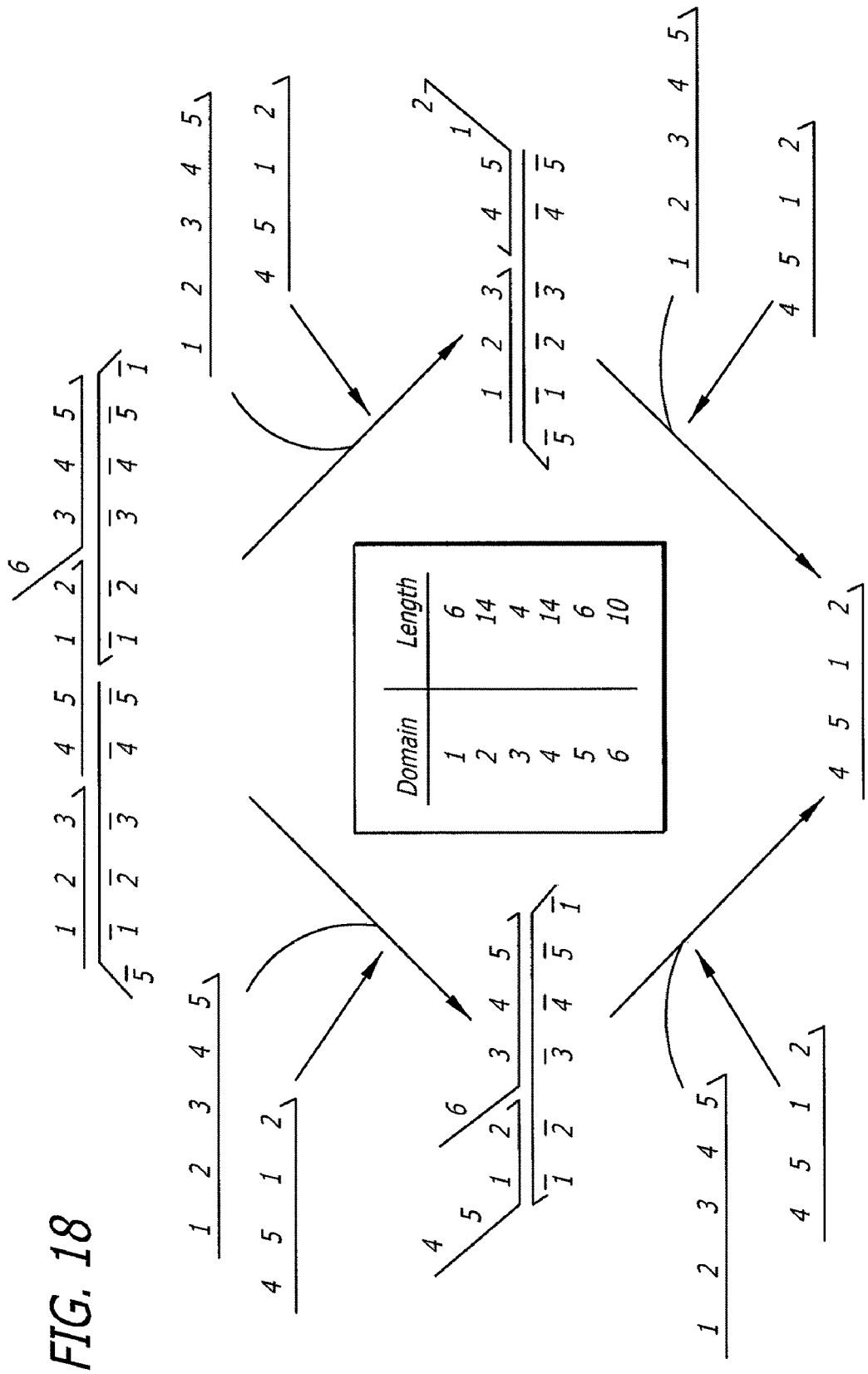
FIG. 18 show schematics of a mechanism for an exemplary super-exponential circuit formed using the toehold DNA catalyst in accordance with one embodiment of the current invention.
Figure 19:
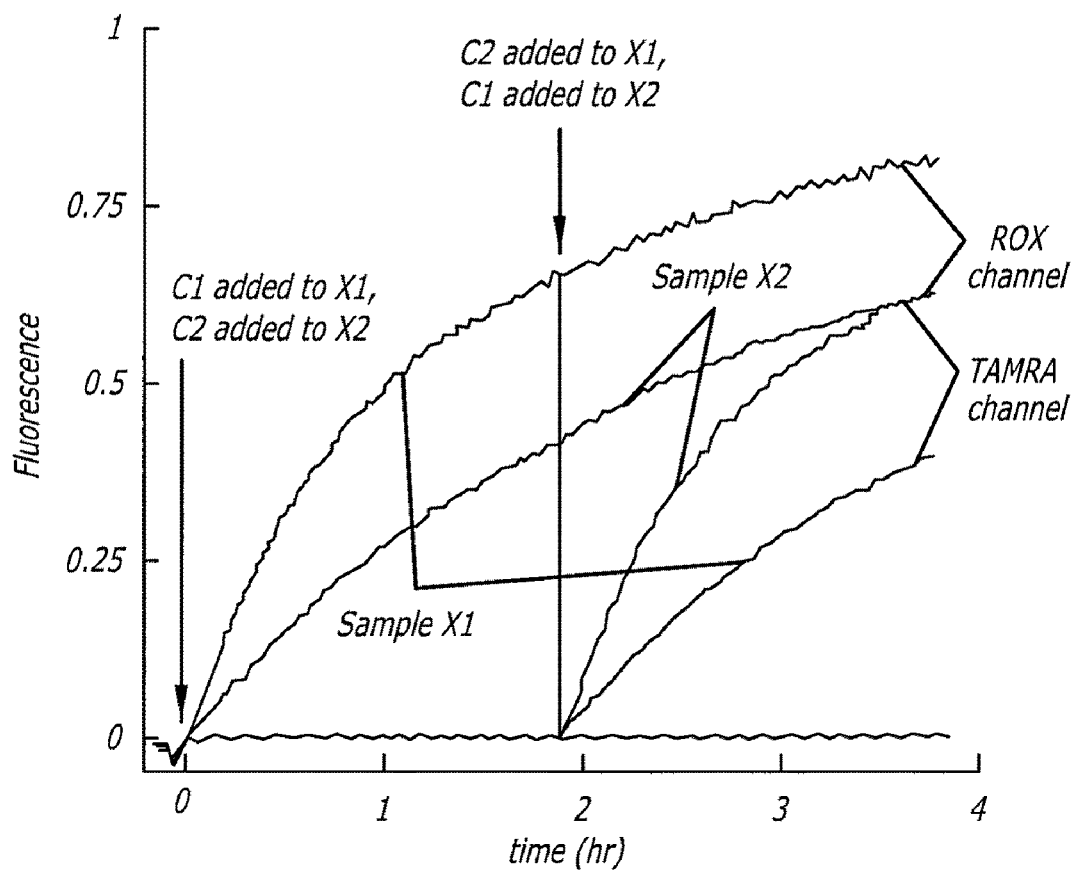
FIG. 19 shows data from an experiment analyzing interference from two independent and simultaneously operating catalyst system in accordance with the current invention.

By combining the ideas of the autocatalyst and the logical AND gate, a simple circuit can be formed that is capable of displaying super-exponential kinetics (see FIG. 18). In the exemplary system shown in FIG. 18, provides a circuit in which a catalytic logic AND gate outputs a molecule which acts as both input elements, demonstrating super-exponential growth kinetics. The super-exponential circuit should possess substantially greater robustness than the exponential autocatalyst circuit, and thus may be a useful alternative for detection and quantitative applications.

CONCLUSION

As shown in the above examples, the novel toehold exchange mechanism used in the catalyst system of the current invention allows a specified input to catalyze the release of a specified output, which in turn can serve as a catalyst for other reactions is provided. This reaction, which can be driven forward by the configurational entropy of the released molecule, provides an amplifying circuit element that is simple, fast, modular, composable, and robust. Using this system it has been possible to construct and characterize several circuits that amplify nucleic acid signals, including a feed-forward cascade with quadratic kinetics and a positive feedback circuit with exponential growth kinetics. Moreover, the system is extremely sensitive. For example, using the feed-forward circuit, 1 pM of DNA can be specifically detected in the course of 12 hours. A minimal autocatalyst is designed as a variant of the catalyst that also exhibits exponential growth. Finally, an allosteric catalyst that can be dynamically switched, and a sigmoidal activation function were also experimentally demonstrated. Because of the flexibility of the catalytic system of the current invention is the availability of numerous potential applications.

One application of being able to engineer an arbitrary sequence into a catalyst is real-time minimally interfering measurement of the concentration of the molecule. For example, in a cell any particular mRNA sequence is constantly being produced and degraded, and the dynamics of its concentration may be of interest. Furthermore, we would not wish to deplete the mRNA in the process of quantitation (e.g. titration versus its complement), as the sequence of interest may be essential to the cell's function/survival. Quantitative PCR (qPCR) has been long used to detect and quantitate specific sequences of DNA and RNA in vitro, but qPCR requires both biologically farmed enzymes and temperature cycling for proper function, thus its application for in vivo systems is not feasible. The quadratic feed-forward circuit provides an intermediate in the tradeoff between operation time and detection sensitivity, and has been experimentally demonstrated to be able to detect 1 pM in the course of 12 hours. A single molecule in a eukaryotic cell volume also corresponds to about 1 pM. Thus, feed-forward circuits with polynomial kinetics may be a reasonable alternative for DNA detection and quantitation.

For scaling up to large circuits, independent catalyst systems must have negligible crosstalk. The success of quantitative models that assume no crosstalk, as presented above, is encouraging; further evidence comes from a test of two independent catalyst systems operating in the same solution. Experimental data from this test is provided in FIG. 19. As shown, the traces show sample (X1) and (X2), monitored in the ROX and TAMRA channel. Fuels for both the system presented in FIG. 5 (F1) and in FIG. 12 (F2) were present in both samples from the beginning. As shown, at t≈0, 10 nM (1×) S1 and S2 were added to both X1 and X2 samples. Additionally, at t≈0, 0.1× C1 was added to X1, while 0.1× C2 was added to X2 in the samples labeled (1). Accordingly, both (1) traces showed increase in fluorescence due to catalytic activity, while the (2) traces show that catalysts C1 and C2 do not possess unwanted catalytic behavior (by catalyzing the other reaction). Control experiments showed that the ROX fluorophore in isolation is detected on the TAMRA channel with brightness 0.1112 relative to signal as detected on the ROX channel. Similarly, the TAMRA fluorophore in isolation produces signal on the ROX channel with efficiency 0.0687 relative to the signal detected on the TAMRA channel. The traces shown in this figure have been adjusted to remove fluorophore channel bleeding (using the datapoints between t=0 and 1.8 hr on the $1^{st}$ and $2^{nd}$ traces as references). At t≈1.8 hr, 0.1× C1 was added to X2, and 0.1× C2 was added to X1. The (1) traces then show increased fluorescence activity, showing that presence of other catalyst systems does not inhibit the proper function of catalysis.

In short, the catalytic systems of the current invention have the potential to avoid the slowdown that plagued previous attempts to construct large nucleic acid circuits. Future nucleic acid control circuits can be interfaced to molecular sensors and actuators. This may be achieved directly when the inputs and outputs are themselves nucleic acids, such as for the detection, analysis, and response to complex nucleic acid samples (Y. Benenson, B. Gil, U. Ben-Dor, R. Adar, E. Shapiro, Nature 429, 423 (2004), the disclosure of which is incorporated herein by reference), or for the control of nucleic acid nanomachines (R. Pei et al., J. Am. Chem. Soc. 128, 12693 (2006), the disclosure of which is incorporated herein by reference). Nucleic acid circuits can also respond to and control more general chemical events: in principle, the release of an oligonucleotide could regulate covalent chemistry by controlling (deoxy)ribozyme activity (9) or reactant proximity. (See, X. Li, D. R. Liu, Angew. Chem. Int. Ed. 43, 4848 (2004), the disclosure of which is incorporated herein by reference.) Additionally, signals carried by small organics and other non-nucleic acid molecules can be read by nucleic acid systems with the use of aptamer domains (A. D. Ellington, J. Szostak, Nature 346, 818 (1990); and J. Tang, R. R. Breaker, Chem. Biol. 4, 453 (1997), the disclosure of which is incorporated herein by reference), and other binding interactions that can regulate toehold accessibility (S. Müller, D. Strohbach, J. Wolf, Proc. IEEE Nanobiotechnol. 153, 31 (2006); and F. J. Isaacs, D. J. Dwyer, J. J. Collins, Nat. Biotechnol. 24, 545 (2006), the disclosure of which is incorporated herein by reference). Thus, nucleic acids could provide a general-purpose system for the synthesis of embedded control circuitry within aqueous chemical systems.

Although examples of a toehold exchange catalyst system and its use have been described and illustrated in detail, it is to be understood that the same is intended by way of illustration and example only and is not to be taken by way of limitation. For example, the invention has been illustrated in the form of a DNA catalyst using specific sequences. However, the toehold exchange catalyst system may be configured with other kinds of sequences or using other kinds of ligands including non-nucleic molecules. Accordingly, variations in and modifications to the toehold exchange catalyst system and its use will be apparent to those of ordinary skill in the art. In most cases, and as will be readily understood by one skilled in the art, alternative configurations of the system may be substituted with small changes, such as, for example, lengths of domains, 5'/3' orientation of molecules, RNA or PNA analogs, etc. Furthermore, throughout the exemplary embodiments, where components are illustrated, these may be substituted as is known in the art within the scope of the invention. The following claims are intended to cover all such modifications and equivalents.

What is claimed is:

1. A toehold exchange catalyst system comprising:
a substrate molecule defining a plurality of binding sites including at least one first toehold binding site that is in an initial, single-stranded state and at least one second toehold binding site that is in an initial, double-stranded state;
a plurality of distinct ligand molecules pre-hybridized onto said substrate molecule, each of said pre-hybridized ligand molecules having binding sites that are complementary to at least one of the plurality of binding sites on said substrate molecule such that the pre-hybridized ligand molecules do not overlap each other, and such that said distinct pre-hybridized ligand molecules jointly occupy all of the plurality of binding sites on said substrate molecule except the first toehold binding site;
a plurality of distinct reactant ligand molecules each of said reactant ligand molecules having binding sites that are complementary to at least one of the plurality of binding sites on said substrate molecule, and wherein at least one of the reactant ligand molecules additionally possesses a binding site complementary to the second toehold binding site;
a catalyst molecule having at least one binding site complementary to the first toehold binding site of the substrate molecule and at least one additional, binding site on said substrate molecule identical, in sequence to the binding sites of at least one of the pre-hybridized ligand molecules on said substrate molecule, but wherein said at least one additional, binding site is not complementary to the second toehold binding site such that when the catalyst molecule is bound to the substrate molecule it triggers an exchange reaction that dislodges at least an output molecule formed from at least one pre-hybridized ligand molecule, thereby converting the second toehold binding site into a single-stranded state; and such that when the second toehold is bound by a reactant ligand molecule the second toehold binding site is converted back into a double-stranded state and the bound catalyst molecule is released thereby converting the first toehold binding site back into a single-stranded state.

2. The system of claim 1, wherein the exchange reaction is driven primarily by center-of-mass configurational, entropy.

3. The system of claim 1, wherein the molecules are selected from the group consisting of small polar organic molecules and polypeptides molecules.

4. The system of claim 1, wherein the substrate molecule, ligand molecule and catalyst molecule are nucleic acid molecules.

5. The system of claim 4, wherein the first toehold site has a length that allows the catalyst molecule to spontaneously dissociate from the substrate molecule in the presence of the reactant ligand molecule.

6. The system of claim 5, wherein both the single-stranded and double-stranded toehold sites have a length of 4 to 10 nucleotides.

7. The system of claim 1, wherein the binding site of at least one of the reactant ligand molecules includes all of the binding sites of at least one of the pre-hybridized ligand molecules on the substrate molecule.

8. The system of claim 1, wherein at least one of the plurality of ligands is a reporter ligand that is detectable when unbound from the substrate molecule by an analytic technique.

9. The system of claim 8, wherein the reporter ligand is fluorescent.

10. The system of claim 1, wherein function of the catalyst molecule is preserved across a range of salt concentrations of from about 0.001 M to 3 M.

11. The system of claim 1, wherein the toehold exchange catalyst system operates across a temperature range of from about 0° C. to 60° C.

12. The system of claim 1, wherein the substrate molecule is provided in a concentration of from about 1 pM and 10 μM.

13. The system of claim 1, further comprising at least one additional, catalyst system, each additional, catalyst system comprising:
at least one additional, substrate molecule;
a plurality of additional, ligand molecules involved with said additional substrate molecule, wherein the output molecule released by the first catalyst system operates as a catalyst molecule for the release of at least one additional, output molecule in the at least one additional, catalyst system.

14. The system of claim 13, wherein the kinetic rate of the catalyst system is quadratic.

15. The system of claim 13, wherein the catalyst molecule of the first catalyst system and the catalyst molecule of the second catalytic system are binding site independent.

16. The system of claim 15, wherein the molecules are nucleic acids and wherein the catalyst molecules are sequence independent.

17. The system of claim 13, wherein the output ligand molecule of the at least one additional, catalytic system either directly or indirectly catalyzes the reaction of the first catalyst system.

18. The system of claim 17, wherein the kinetic rate of the catalysis is exponential.

19. The system of claim 1, wherein the output molecule has a sequence that includes the sequence of at least the catalyst molecule.

20. The system of claim 19, wherein the toehold exchange catalyst system has an initial, kinetic rate that is exponentially growing.

21. The system of claim 1, wherein the catalyst molecule is allosteric such that it is switched between at least two states by the presence of at least one activator molecule, and wherein each of the at least two states possesses different catalytic properties.

22. The system of claim 21, wherein the at least two of the states are an active catalytic and an inactive catalytic state.

23. The system of claim 21, wherein the catalyst molecule catalyzes different reactions depending on the state of the catalyst molecule.

24. The system of claim 21, wherein the catalyst molecule is a single-stranded molecule of DNA that adopts two different hairpin conformations, such that at least one portion of each catalytic region is protected in a double-stranded binding geometry in each catalyst folding state.

25. The system of claim 21, wherein the activator molecule is the output molecule of an independent catalyzed reaction.

26. The system of claim 1, wherein the catalyst system is designed as a catalytic logic gate.

27. The system of claim 26, wherein the logic gate is one of either an AND or an OR gate.

28. The system of claim 27, wherein the logic gate is an AND gate comprising at least two independent catalyst molecules, and wherein the desired output molecule is bound to the substrate molecule such that both of the at least two independent catalyst molecules must react with the substrate molecule to release the output molecule.

29. The system of claim 28, wherein the output molecule of the catalytic logic AND gate is capable of functioning as both of the at least two independent catalyst molecules.

30. The system of claim 29, wherein the kinetic rate of the catalysis is super-exponential.

31. The system of claim 26, wherein the logical, gate is an OR gate comprising at least two independent catalyst molecules, and wherein the desired output molecule is bound to the substrate molecule such that the output molecule is released when either of the at least two independent catalyst molecules reacts with the substrate molecule.

32. The system of claim 26, comprising a plurality of catalyst systems wherein the output molecule of the catalytic logic gate serves as a catalytic input for a further reaction.

33. The system of claim 32, wherein the further reaction comprises at least one additional, catalytic logic gate.

34. Catalyzing a reaction through a toehold exchange comprising:
providing a substrate molecule defining a plurality of binding sites including at least one first toehold binding site that is in an initial, single-stranded state and at least one second toehold binding site that is in an initial, double-stranded state;
providing a plurality of distinct ligand molecules, each of said ligand molecules having binding sites that are complementary to at least one of the plurality of binding sites on said substrate molecule;
pre-hybridizing at least one of said ligand molecules onto said substrate molecule such that the at least one pre-hybridized ligand molecules occupies all of the plurality of binding sites on said substrate molecule except the first toehold binding site;
providing a plurality of distinct reactant ligand molecules each of said reactant ligand molecules having cooperative binding sites on said substrate molecule, wherein the binding sites are complementary to at least one of the plurality of binding sites on said substrate molecule, and wherein at least one of the reactant ligand molecules additionally possesses a binding site complementary to the second toehold binding site;

introducing a catalyst molecule, said catalyst molecule having at least one binding site complementary to the first toehold binding site of the substrate molecule, and at least one additional, binding site on the substrate molecule identical, in sequence to the binding sites of at least one of the pre-hybridized ligand molecules on said substrate molecule, but wherein said at least one additional, binding site is not complementary to the second toehold binding site;

triggering an exchange reaction by binding the catalyst molecule with the substrate molecule whereby at least an output molecule is dislodged, the output molecule formed from at least one pre-hybridized ligand molecule, thereby converting the second toehold binding site into a single-stranded state;

binding a reactant ligand molecule to the second toehold binding site thereby converting the second toehold binding site back into a double-stranded state and releasing at least the bound catalyst molecule, thereby converting the first toehold binding site back into a single-stranded state; and monitoring the release of the output molecule.

35. The method of claim 34, wherein the exchange reaction is driven primarily by the entropy gain of the pre-hybridized ligand molecules released from the substrate.

36. The method of claim 34, wherein the catalyst molecule of a catalyzed reaction is a synthetic or naturally occurring DNA or mRNA molecule, and further comprising determining the concentration of the catalyst molecule by monitoring the rate of production of the output molecule to provide real-time detection and quantitation of DNA and mRNA concentrations in the system.

37. The system of claim 4, wherein the second toehold site has a length that allows the pre-hybridized ligand molecule to spontaneously dissociate from the substrate molecule in the presence of the catalyst molecule.

* * * * *

UNITED STATES PATENT AND TRADEMARK OFFICE
CERTIFICATE OF CORRECTION

PATENT NO. : 8,110,353 B2
APPLICATION NO. : 12/025652
DATED : February 7, 2012
INVENTOR(S) : David Zhang It is certified that error appears in the above-identified patent and that said Letters Patent is hereby corrected as shown below:

Column 27, Claim 1, line 54, delete "," after the word "initial".
Column 27, Claim 1, line 55, delete "," after the word "initial".
Column 27, Claim 1, line 57, delete "," after the word "additional".
Column 27, Claim 1, line 58, delete "," after the word "identical".
Column 27, Claim 1, line 61, delete "," after the word "additional".
Column 29, Claim 2, line 7, delete "," after the word "configurational".
Column 29, Claim 11, line 38, delete "." before the word "to".
Column 29, Claim 13, line 42, delete "," after the word "additional".
Column 29, Claim 13, line 42, delete "," after the word "additional".
Column 29, Claim 13, line 44, delete "," after the word "additional".
Column 29, Claim 13, line 45, delete "," after the word "additional".
Column 29, Claim 13, line 49, delete "," after the word "additional".
Column 29, Claim 13, line 49, delete "," after the word "additional".
Column 29, Claim 17, line 60, delete "," after the word "additional".
Column 30, Claim 20, line 2, delete "," after the word "initial".
Column 30, Claim 31, line 36, delete "," after the word "logical".
Column 30, Claim 33, line 46, delete "," after the word "additional".
Column 30, Claim 34, line 51, delete "," after the word "initial".
Column 30, Claim 34, line 52, delete "," after the word "initial".
Column 30, Claim 34, line 60, delete "molecules" and add --molecule--.
Column 31, Claim 34, line 6, delete "," after the word "additional".
Column 31, Claim 34, line 7, delete "," after the word "initial".

Page 1 of 1

Signed and Sealed this
Fifth Day of March, 2013

Teresa Stanek Rea
*Acting Director of the United States Patent and Trademark Office*

SEQUENCE LISTING

<160> NUMBER OF SEQ ID NOS: 16

<210> SEQ ID NO 1
<211> LENGTH: 10
<212> TYPE: DNA
<213> ORGANISM: Artificial sequence
<220> FEATURE:
<223> OTHER INFORMATION: Synthetically produced sequence

<400> SEQUENCE: 1
ctttcctaca                                                          10

<210> SEQ ID NO 2
<211> LENGTH: 12
<212> TYPE: DNA
<213> ORGANISM: Artificial sequence
<220> FEATURE:
<223> OTHER INFORMATION: Synthetically produced sequence

<400> SEQUENCE: 2
actaacttac gg                                                       12

<210> SEQ ID NO 3
<211> LENGTH: 16
<212> TYPE: DNA
<213> ORGANISM: Artificial sequence
<220> FEATURE:
<223> OTHER INFORMATION: Synthetically produced sequence

<400> SEQUENCE: 3
cattcaatac cctacg                                                   16

<210> SEQ ID NO 4
<211> LENGTH: 16
<212> TYPE: DNA
<213> ORGANISM: Artificial sequence
<220> FEATURE:
<223> OTHER INFORMATION: Synthetically produced sequence

<400> SEQUENCE: 4
ccacatacat catatt                                                   16

<210> SEQ ID NO 5
<211> LENGTH: 10
<212> TYPE: DNA
<213> ORGANISM: Artificial sequence
<220> FEATURE:
<223> OTHER INFORMATION: Synthetically produced sequence

```
<400> SEQUENCE: 5
cattcaatac                                                          10

<210> SEQ ID NO 6
<211> LENGTH: 12
<212> TYPE: DNA
<213> ORGANISM: Artificial sequence
<220> FEATURE:
<223> OTHER INFORMATION: Synthetically produced sequence

<400> SEQUENCE: 6
tacttattag cc                                                       12

<210> SEQ ID NO 7
<211> LENGTH: 10
<212> TYPE: DNA
<213> ORGANISM: Artificial sequence
<220> FEATURE:
<223> OTHER INFORMATION: Synthetically produced sequence

<400> SEQUENCE: 7
ctactttcac                                                          10

<210> SEQ ID NO 8
<211> LENGTH: 44
<212> TYPE: DNA
<213> ORGANISM: Artificial sequence
<220> FEATURE:
<223> OTHER INFORMATION: Synthetically produced sequence

<400> SEQUENCE: 8
accacatcaa tctcgatcca gtacacctct tcacgaacat ttca                    44

<210> SEQ ID NO 9
<211> LENGTH: 50
<212> TYPE: DNA
<213> ORGANISM: Artificial sequence
<220> FEATURE:
<223> OTHER INFORMATION: Synthetically produced sequence

<400> SEQUENCE: 9
tggctatgaa atgttcgtga agaggtgtac tggatcgaga ttgatgtggt              50

<210> SEQ ID NO 10
<211> LENGTH: 20
<212> TYPE: DNA
<213> ORGANISM: Artificial sequence
<220> FEATURE:
<223> OTHER INFORMATION: Synthetically produced sequence

<400> SEQUENCE: 10
acctcttcac gaacatttca                                               20

<210> SEQ ID NO 11
<211> LENGTH: 34
<212> TYPE: DNA
<213> ORGANISM: Artificial sequence
<220> FEATURE:
<223> OTHER INFORMATION: Synthetically produced sequence

<400> SEQUENCE: 11
acctaatagc accacatcaa tctcgatcca gtac                               34

<210> SEQ ID NO 12
<211> LENGTH: 22
```

```
<212> TYPE: DNA
<213> ORGANISM: Artificial sequence
<220> FEATURE:
<223> OTHER INFORMATION: Synthetically produced sequence

<400> SEQUENCE: 12
cttcacgaac atttcatagc ca                                           22

<210> SEQ ID NO 13
<211> LENGTH: 20
<212> TYPE: DNA
<213> ORGANISM: Artificial sequence
<220> FEATURE:
<223> OTHER INFORMATION: Synthetically produced sequence

<400> SEQUENCE: 13
acctaatagc accacatcaa                                              20

<210> SEQ ID NO 14
<211> LENGTH: 27
<212> TYPE: DNA
<213> ORGANISM: Artificial sequence
<220> FEATURE:
<223> OTHER INFORMATION: Synthetically produced sequence

<400> SEQUENCE: 14
atcgagattg atgtggtgct attaggt                                      27

<210> SEQ ID NO 15
<211> LENGTH: 16
<212> TYPE: DNA
<213> ORGANISM: Artificial sequence
<220> FEATURE:
<223> OTHER INFORMATION: Synthetically produced sequence

<400> SEQUENCE: 15
acttcagtca ttaagc                                                  16

<210> SEQ ID NO 16
<211> LENGTH: 14
<212> TYPE: DNA
<213> ORGANISM: Artificial sequence
<220> FEATURE:
<223> OTHER INFORMATION: Synthetically produced sequence

<400> SEQUENCE: 16
ccatacaagt atca                                                    14
```